United States Patent
Hasson et al.

(12) 
(10) Patent No.: US 6,430,939 B2
(45) Date of Patent: Aug. 13, 2002

(54) HYPERPOLARIZED GAS CONTAINERS, SOLENOIDS, TRANSPORT AND STORAGE DEVICES AND ASSOCIATED TRANSPORT AND STORAGE METHODS

(75) Inventors: Kenton C. Hasson, Durham; Geri T. K. Zollinger; David L. Zollinger, both of Chapel Hill; Paul L. Bogorad, Hillsborough; Bradley A. Wheeler, Raleigh, all of NC (US)

(73) Assignee: Medi-Physics, Inc., Princeton, NJ (US)

( * ) Notice: Subject to any disclaimer, the term of this patent is extended or adjusted under 35 U.S.C. 154(b) by 0 days.

(21) Appl. No.: 09/846,720

(22) Filed: May 1, 2001

Related U.S. Application Data

(62) Division of application No. 09/333,571, filed on Jun. 16, 1999.
(60) Provisional application No. 60/121,315, filed on Feb. 23, 1999, and provisional application No. 60/089,692, filed on Jun. 17, 1998.

(51) Int. Cl.[7] .............................................. F17C 13/02
(52) U.S. Cl. ........................ 62/49.1; 600/420; 604/20; 604/181
(58) Field of Search ................................ 336/178–182; 335/251–7; 62/49.1, 48.1, 27, 600, 914, DIG. 1; 600/420; 604/26, 181

(56) References Cited

U.S. PATENT DOCUMENTS 5,418,513 A * 5/1995 Fujisawa et al. ............ 336/178
5,617,859 A * 4/1997 Souza et al. ................ 324/309

* cited by examiner

*Primary Examiner*—Lincoln Donovan
(74) *Attorney, Agent, or Firm*—Myers Bigel Sibley & Sajovec, P.A.

(57) ABSTRACT

A compact portable transport unit for shipping hyperpolarized noble gases and shielding same from electromagnetic interference and/or external magnetic fields includes a means for shifting the resonance frequency of the hyperpolarized gas outside the bandwidth of typical frequencies associated with prevalent time-dependent fields produced by electrical sources. Preferably the transport unit includes a magnetic holding field which is generated from a solenoid in the transport unit. The solenoid includes a plurality of coil segments and is sized and configured to receive the gas chamber of a container. The gas container is configured with a valve, a spherical body, and an extending capillary stem between the valve and the body. The gas container or hyperpolarized product container can also be formed as a resilient bag. The distribution method includes positioning a multi-bolus container within the transport unit to shield it and transporting same to a second site remote from the first site and subsequently dispensing into smaller patient sized formulations which can be transported (shielded) in another transport unit to yet another site.

48 Claims, 18 Drawing Sheets

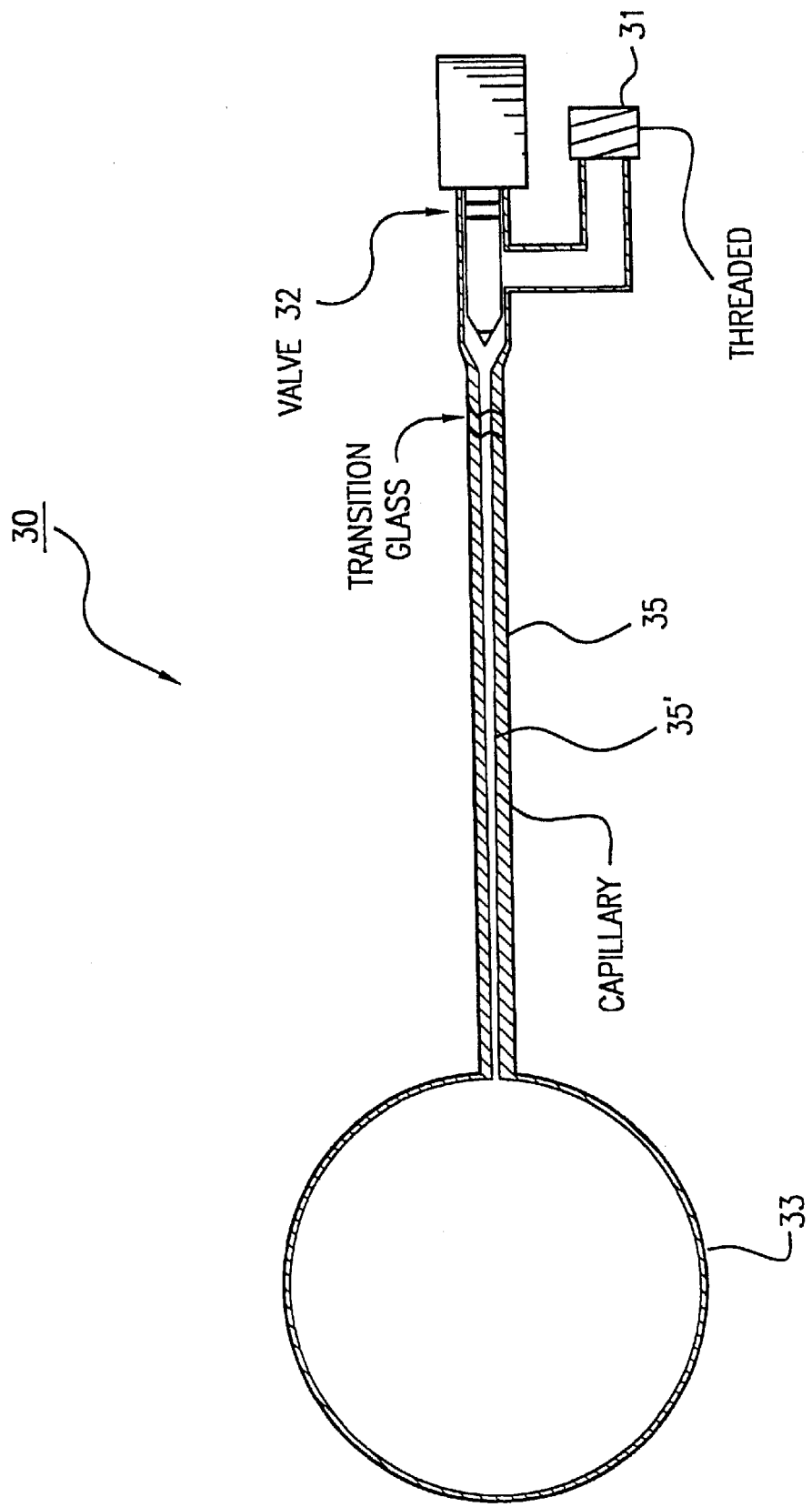

HYPERPOLARIZED GAS CONTAINERS, SOLENOIDS, TRANSPORT AND STORAGE DEVICES AND ASSOCIATED TRANSPORT AND STORAGE METHODS

RELATED APPLICATIONS

This application is a divisional of U.S. patent application Ser. No. 09/333,571 filed Jun. 16, 1999, which claims the benefit of priority from Provisional Application No. 60/089,692, filed Jun. 17, 1998, entitled "Containers for Hyperpolarized Gases and Associated Methods" and Provisional Application No. 60/121,315, filed Feb. 2, 1999, entitled "Hyperpolarized Gas Containers, Solenoids, and Transport and Storage Devices and Associated Transport and Storage Methods." The contents of these applications are hereby incorporated by reference as if recited in full herein.

GOVERNMENT RIGHTS

This invention was made with Government support under National Institute of Health Grant No. R43HL62756-01. The United States Government has certain rights in this invention.

FIELD OF THE INVENTION

The present invention relates generally to the transport of hyperpolarized gases from one site to another, such as from a production site to a clinical use site. The hyperpolarized gases are particularly suitable for MR imaging and spectroscopy applications.

BACKGROUND OF THE INVENTION

Inert gas imaging ("IGI") using hyperpolarized noble gases is a promising recent advance in Magnetic Resonance Imaging (MRI) and MR spectroscopy technologies. Conventionally, MRI has been used to produce images by exciting the nuclei of hydrogen molecules (present in water protons) in the human body. However, it has recently been discovered that polarized noble gases can produce improved images of certain areas and regions of the body which have heretofore produced less than satisfactory images in this modality. Polarized Helium-3 ("$^3$He") and Xenon-129 ("$^{129}$Xe") have been found to be particularly suited for this purpose. Unfortunately, as will be discussed further below, the polarized state of the gases is sensitive to handling and environmental conditions and can, undesirably, decay from the polarized state relatively quickly.

Various methods may be used to artificially enhance the polarization of certain noble gas nuclei (such as $^{129}$Xe or $^3$He) over the natural or equilibrium levels, i.e., the Boltzmann polarization. Such an increase is desirable because it enhances and increases the MRI signal intensity, allowing physicians to obtain better images of the substance in the body. See U. S. Pat. No. 5,545,396 to Albert et al., the disclosure of which is hereby incorporated by reference as if recited in full herein.

A "$T_1$" decay time constant associated with the longitudinal relaxation of the hyperpolarized gas is often used to characterize the length of time it takes a gas sample to depolarize in a given situation. The handling of the hyperpolarized gas is critical because of the sensitivity of the hyperpolarized state to environmental and handling factors and thus the potential for undesirable decay of the gas from its hyperpolarized state prior to the planned end use, e.g., delivery to a patient for imaging. Processing, transporting, and storing the hyperpolarized gases—as well as delivering the gas to the patient or end user—can expose the hyperpolarized gases to various relaxation mechanisms such as magnetic field gradients, surface-induced relaxation, hyperpolarized gas atom interactions with other nuclei, paramagnetic impurities, and the like.

One way of minimizing the surface-induced decay of the hyperpolarized state is presented in U.S. Pat. No. 5,612,103 to Driehuys et al. entitled "Coatings for Production of Hyperpolarized Noble Gases." Generally stated, this patent describes the use of a modified polymer as a surface coating on physical systems (such as a Pyrex™ container) which contact the hyperpolarized gas to inhibit the decaying effect of the surface of the collection chamber or storage unit. Other methods for minimizing surface or contact-induced decay are described in co-pending and co-assigned U.S. patent application Ser. No. 09/163,721 to Zollinger et al., entitled "Hyperpolarized Noble Gas Extraction Methods, Masking Methods, and Associated Transport Containers," and co-pending and co-assigned U.S. patent application identified by Attorney Docket No. 5770-12IP, entitled "Resilient Containers for Hyperpolarized Gases and Associated Methods." The contents of these applications are hereby incorporated by reference as if recited in full herein.

However, other relaxation mechanisms arise during production, handling, storage, and transport of the hyperpolarized gas. These problems can be particularly troublesome when storing the gases (especially increased quantities) or transporting the hyperpolarized gas from a production site to a (remote) use site. In transit, the hyperpolarized gas can be exposed to many potentially depolarizing influences. In the past, a frozen amount of hyperpolarized $^{129}$Xe (about 300 cc–500 cc's) was collected in a cold finger and positioned in a metallic coated dewar along with a small yoke of permanent magnets arranged to provide a magnetic holding field therefor. The frozen gas was then taken to an experimental laboratory for delivery to an animal subject. Unfortunately, the permanent magnet yoke provided a relatively small magnetic field region (volume) with a relatively low magnetic homogeneity associated therewith. Further, the thawed sample yielded a relatively small amount of useful hyperpolarized $^{129}$Xe (used for small animal subjects) which would not generally be sufficient for most human sized patients.

There is, therefore, a need to provide improved ways to transport hyperpolarized gases so that the hyperpolarized gas is not unduly exposed to depolarizing effects during transport. Improved storage and transport methods and systems are desired so that the hyperpolarized product can retain sufficient polarization and larger amounts to allow effective imaging at delivery when stored or transported over longer transport distances in various (potentially depolarizing) environmental conditions, and for longer time periods from the initial polarization than has been viable previously.

OBJECTS AND SUMMARY OF THE INVENTION

It is therefore an object of the present invention to provide a transport system that can protect hyperpolarized gas products from potentially depolarizing environmental exposures during movement of the hyperpolarized gas products from a production site to a remote use site.

It is also an object of the present invention to configure a transport unit to serve alternatively or in addition as a portable storage unit, to hold polarized gases in their polarized state for longer periods including prior to shipment, or prior to delivery even if the gases are not intended to be remotely shipped.

It is also an object of the present invention to provide a portable unit for storing or transporting a quantity of hyperpolarized gas therein, which can substantially protect the hyperpolarized gas from the depolarizing effect of diffusion of the gas atoms through magnetic field gradients.

It is another object of the present invention to provide a portable unit for storing or transporting a quantity of hyperpolarized gas therein, which can substantially protect the hyperpolarized gas from the depolarizing effects of one or more of oscillating magnetic fields, electromagnetic noise, and electromagnetic interference (EMI).

It is another object of the present invention to provide a method of protecting the hyperpolarized gas from the depolarizing effects of undesirable EMI at a predetermined frequency or frequency range.

It is another object of the invention to provide a relatively compact, lightweight, easily transportable device which can provide sufficient protection for the hyperpolarized gas to allow the hyperpolarized gas to be successfully transported (such as in a vehicle) from a production site to a remote use site, such that the hyperpolarized gas retains a sufficient level of polarization at the use site to allow for clinically useful images.

It is another object of the invention to provide a valved hyperpolarized gas chamber configured to inhibit polarization decay (i.e., has relatively long decay times) during transport and/or storage.

It is another object of the invention to configure a transport unit to minimize the external force associated with shock, vibration, and or other mechanical collisions that are input into or transmitted to the hyperpolarized gas container.

It is another object of the invention to provide a protective enclosure for a transport unit which is configured such that the hyperpolarized gas held in an internally disposed hyperpolarized gas chamber may be directed out of or into the transport unit (i.e., the gas chamber may be filled and/or emptied), without the need to remove the gas chamber from its protective housing.

It is another object of the invention to configure a transport unit with an easily accessible means for interrogating the polarized gas held within the gas chamber held therein using nuclear magnetic resonance (NMR), in order to measure the polarization of the gas, or to measure the decay rate of the polarization.

It is another object of the invention to provide a means of adjusting the magnetic field strength generated by a transport unit, in order to shift the Larmor frequency of the spins associated with the hyperpolarized gas, either for purposes of NMR measurements, or to minimize decay from electromagnetic interference at a frequency of interest.

It is an additional object of the present invention to increase the shielding effectiveness of transport units.

It is still another object of the invention to provide a way to transport hyperpolarized gases from a polarization site to a secondary and/or tertiary distribution site while maintaining a sufficient level of hyperpolarization to allow clinically useful images at the ultimate use site.

These and other objects of the present invention are provided by the transport (and/or storage) units of the instant invention which are configured to protect hyperpolarized gas (and gas products and in one or multiple containers) held therein, thereby minimizing depolarizing losses introduced during transport of a hyperpolarized gas product from one place to another. In particular, a first aspect of the invention is directed toward a transport unit used to transport hyperpolarized products therein. The transport unit comprises at least one gas chamber configured to hold a quantity of hyperpolarized product therein and at least one electromagnet providing a magnetic holding field defining at least one region of homogeneity. The homogeneous region of the magnetic holding field is sized and configured to receive a major portion of the gas chamber (gas holding container) therein. The magnetic holding field is preferably primarily provided by a solenoid comprising at least one current carrying wire thereon. In one embodiment, the gas chamber is defined by a rigid body single or multi-dose container. In an alternative embodiment, the gas chamber is defined by a resilient body container with an expandable gas chamber (preferably sized and configured to hold a single patient dose).

In one preferred embodiment, a solenoid coil is configured to generate the magnetic holding field. Preferably the solenoid coil is also sized and configured to maximize the volume of the sufficiently homogeneous region provided thereby. Also preferably, the transport unit preferably includes one or more layers of an electrically conducting metal about the enclosure. As such, the enclosure can provide shielding from external electromagnetic radiation as well as mechanical support and protection. The transport unit may also include one or more layers of magnetically permeable materials, such as soft iron or mu-metal, to provide additional electromagnetic shielding, (including DC magnetic shielding), or to act as a flux return.

A further aspect of the present invention is a solenoid coil for providing a homogeneous magnetic field region in which the hyperpolarized gas is held. The solenoid comprises a cylindrical body and a first coil segment having a first coil length and a first number of windings disposed on the cylindrical body. The solenoid also includes second and third coil segments having respective second and third coil lengths and respective second and third number of windings disposed on the cylindrical body. The first, second, and third coil segments are spatially separated and positioned on the cylindrical body such that the second coil segment is intermediate the first and third coil segments. In a preferred embodiment, the second coil length is greater than both of the first and third coil lengths and the first and third windings are configured with a greater number of layers relative to the second winding. This coil configuration can advantageously provide a larger sufficiently homogeneous holding region for the hyperpolarized gas within a relatively compact coil area, thereby allowing the coil (as well as any associated transport unit) itself to be more compact while also providing for a useful dose of the hyperpolarized gas to be contained and protected therein.

Another aspect of the present invention is a hyperpolarized gas product container having a gas holding chamber and a capillary stem. The capillary stem has an inner diameter and length configured and sized such that the capillary stem preferably inhibits the migration or diffusional exchange of the hyperpolarized gas product between the main body of the chamber and the upper portion of the gas container which preferably includes a valve. More specifically, the capillary stem is sized such that the ratio of the main body volume to the volume in the capillary stem, multiplied by the diffusion time for $^3$He to traverse the length of the capillary, is greater than the $T_1$ of a sealed chamber of the same material and dimensions. Exchange of gas product between the main body and the valve is udesirable because the valve is typically in a region of higher magnetic field gradients. Further, the valve may comprise materials that can undesirably introduce surface-induced relaxation into the polarized gas. The container itself may be configured as a rigid body or resilient body.

Yet another aspect of the present invention is a transport unit including at least one resilient container (and preferably a plurality of resilient containers) for holding a quantity of hyperpolarized gas (or liquid) product therein. In operation, one or more of the resilient containers are positionable within a homogeneous region of a magnetic field produced by the transport and/or storage unit.

Another aspect of the present invention is a system for distributing hyperpolarized gases, and preferably patient sized doses of hyperpolarized gases. The system includes a first transport unit which is sized and configured to hold a large multi-dose container therein. The system also includes at least one second transport unit sized and configured to carry a plurality of single dose containers therein. Preferably, the multi-dose container is a rigid body container and the single dose containers are resilient containers having expandable chambers to allow easy delivery or administration at a use site.

Similarly, in one embodiment, the multi-dose container is transported to a pharmaceutical distribution point where the hyperpolarized gas in the multi-dose container can be formulated into the proper dosage or mixture according to standard pharmaceutical industry operation. This may include solubilizing the gas, adjusting the concentration, preparing the mixture for injection or inhalation or other administration as specified by a physician, or combining two different gases or liquids or other substances with the transported hyperpolarized gas. Then, the formulated hyperpolarized product, substance, or mixture is preferably dispensed into at least one second container, and preferably into a plurality of preferably a single use size resilient containers which can be transported to a third or tertiary site for use. In a preferred embodiment, the first transport distance is such that the hyperpolarized gas is moved at increased times or distances over conventional uses. Preferably, the transport units and associated container of the present invention are configured such that during transport and/or storage, the hyperpolarized gas (particularly $^3$He) retains sufficient polarization after about 10 hours from polarization, and preferably after at least 14 hours, and still more preferably (especially for $^3$He) after about 30 hours. Stated differently, the transport units and associated containers of the instant invention allow clinical use after about 30 hours elapsed time from original polarization and after transport to a second site (and even then a third or tertiary site). The transporters and containers are also preferably configured to allow greater transit distances or greater transit times. Stated differently, the hyperpolarized product retains sufficient polarization after transport and greater elapsed time from polarization when positioned in the transport units to provide clinically useful images. This distribution system is in contrast to the conventional procedure, whereby the hyperpolarized gas is produced at a polarization site and rushed to a use site (which is typically relatively close to the polarization site).

An additional aspect of the present invention is directed toward a method of minimizing the relaxation rate of hyperpolarized noble gases due to external electromagnetic interference. The method includes the steps of capturing a quantity of hyperpolarized gas in a transportable container and shifting the resonant frequency of the hyperpolarized noble gas out of the frequency range of predetermined electromagnetic interference. Preferably, the method includes shifting the normal resonance frequency associated with the hyperpolarized gas to a frequency substantially outside the bandwidth of prevalent time-dependent fields produced by electrically powered equipment (such as computer monitors), vehicular engines, acoustic vibrations, and other sources. In a preferred embodiment, the resonant frequency of the hyperpolarized gas is shifted by applying a static magnetic field proximate to the hyperpolarized gas. For example, preferably for a hyperpolarized gas product comprising $^3$He, the applied static magnetic field is at least about 7 Gauss, while for hyperpolarized gas products comprising $^{129}$Xe, the applied magnetic field is at least about 20 Gauss.

Yet another aspect of the present invention is directed toward a system for preserving the polarization of the gas during transport. The system includes the steps of introducing a quantity of hyperpolarized gas product into a sealable container comprising a gas chamber at a production site and capturing a quantity of hyperpolarized gas product in the gas chamber. A magnetic holding field is generated by a portable transport unit defining a substantially homogeneous magnetic holding region therein. The gas chamber is positioned within the homogeneous holding region and the hyperpolarized gas product is shielded to minimize the depolarizing effects of external magnetic fields such that the hyperpolarized gas has a clinically useful polarization level at a site remote from the production site.

In a preferred embodiment, the step of providing the magnetic holding field is performed by electrically activating a longitudinally-extending solenoid positioned in the transport unit. The solenoid comprises a plurality of spatially separated coil segments, and the sealable container comprises a capillary stem in fluid communication with the gas chamber.

The present invention is advantageous because the transport unit can protect the hyperpolarized gas and minimize the depolarizing effects attributed to external magnetic fields, especially deleterious oscillating fields, which can easily dominate other relaxation mechanisms. The transport container is relatively compact and is, thus, easily portable. Preferably, the transport unit includes a homogeneous magnetic holding field positioned proximate to the gas container so that it provides adequate protection for the hyperpolarized state of the gas and facilitates the transport of the gas to an end use site. In a preferred embodiment, the transport unit includes a solenoid having at least a three-coil segment configuration with the central coil segment having a reduced number of wire layers compared to the other (opposing) two coil segments. Stated differently, the opposing end segments have a greater number of wire layers providing increased current density (current per unit length) in these areas. Advantageously, such a coil segment design can enlarge the homogeneous region of the magnetic field generated by the solenoid while minimizing the size (length) of the solenoid itself. This relatively compact transport unit can easily deliver a single patient dose or a plurality of patient doses (combined or individual).

Further, the transport unit is configured such that it can use an adjustable current to allow field adjustments, thereby enabling correction for one or more of electronic or mechanical drift, the type of gas transported, and severe exposure conditions. In addition, the transport unit can be employed with more than one type of hyperpolarized gas, for example, $^3$He or $^{129}$Xe. In addition, the transport unit can be configured such that the hyperpolarized gas can be released at the end use site without removing the typically somewhat fragile gas chamber from the transport unit (when glass chambers are employed). This capability can protect the gas from intermediate depolarizing handling and can also facilitate the safe release of the gas by shielding any users proximate to the transport unit from exposure to the internal gas container (such as a glass sphere) which is typically under relatively high pressure. Alternatively, the transport unit can shield resiliently configured gas containers to provide easy to dispense single dose sized products. In addition, the gas container preferably includes a capillary stem and/or a port isolation means which inhibits the diffusion or movement of the hyperpolarized gas out of the main body, thereby helping to retain a majority of the hyperpolarized gas within the homogeneous holding region and inhibiting contact between the hyperpolarized gas and the potentially depolarizing materials in the sealing means. Further, the enclosure walls of the instant invention are preferably configured such that they provide adequate spatial separation from the gas container to increase the shielding effectiveness of the transport unit.

BRIEF DESCRIPTION OF THE DRAWINGS

FIG. 4 is a side view of a gas chamber configuration particularly suitable for use with the transport unit according to the present invention.

DETAILED DESCRIPTION OF THE INVENTION

Figure 1:
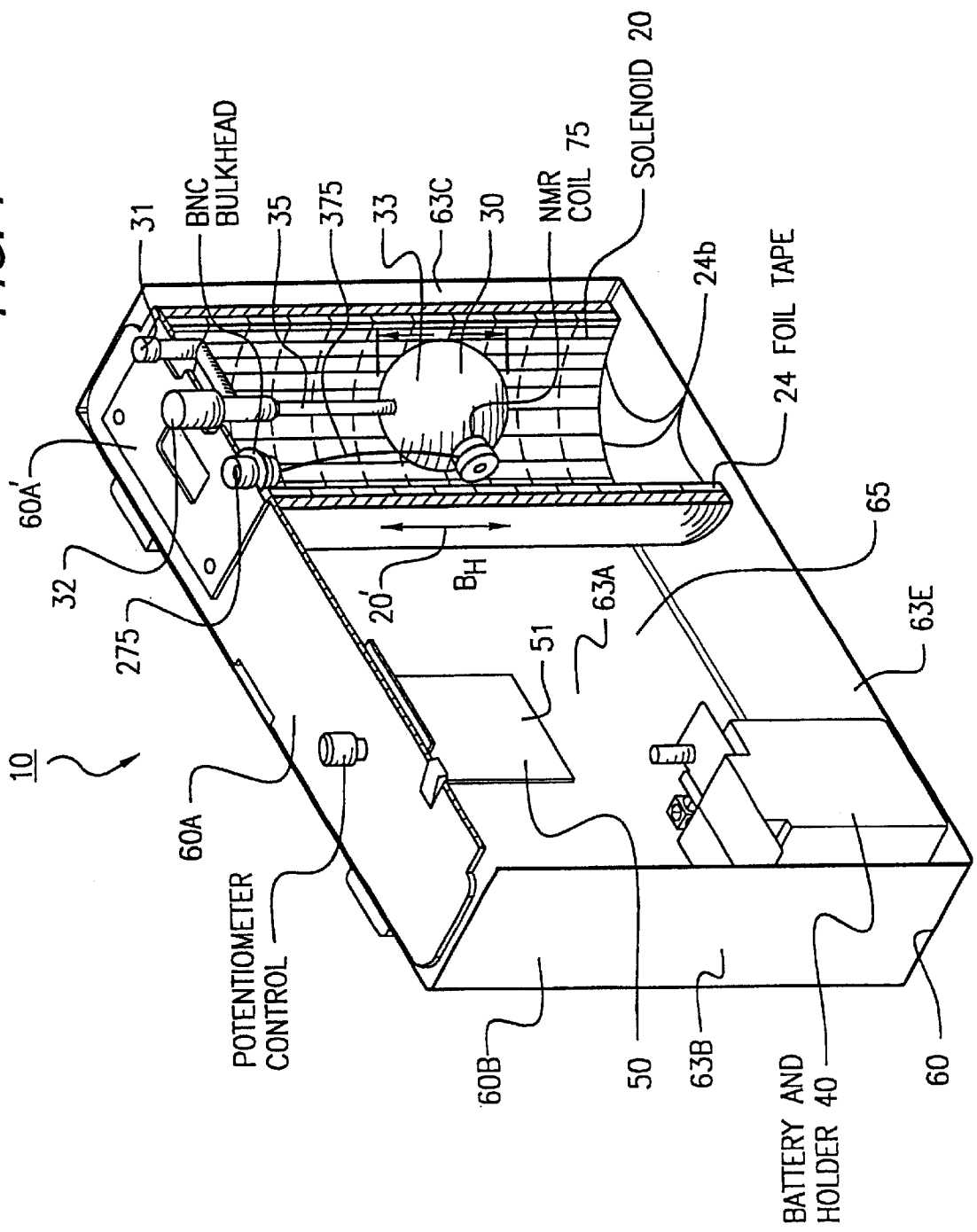
FIG. 1 is a cutaway front perspective view of a transport unit according to the present invention, the transport unit comprising a gas chamber and solenoid.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, layers and regions may be exaggerated for clarity.

For ease of discussion, the term "hyperpolarized gas" is used to describe a hyperpolarized gas alone, or a hyperpolarized gas that contacts or combines with one or more other components, whether gaseous, liquid, or solid. Thus, the hyperpolarized gas described herein can be a hyperpolarized gas composition/mixture (preferably non-toxic such that it is suitable for in vivo administration) such that the hyperpolarized gas can be combined with other gases and/or other inert or active substances or components. Also, as used herein, the term "hyperpolarized gas" can include a product in which the hyperpolarized gas is dissolved into another liquid (such as a carrier fluid) or processed such that it transforms into a substantially liquid state, i.e., "a liquid polarized gas". In summary, as used herein, the term "gas" has been used in certain places to descriptively indicate a noble gas which has been hyperpolarized and which can include one or more components and which may be present in or further processed to be in one or more physical forms.

Background—Hyperpolarization

Various techniques have been employed to polarize, accumulate and capture polarized gases. For example, U.S. Pat. No. 5,642,625 to Cates et al. describes a high volume hyperpolarizer for spin-polarized noble gas and U.S. Pat. No. 5,642,625 to Cates et al. describes a cryogenic accumulator for spin-polarized $^{129}$Xe. The disclosures of this patent and application are hereby incorporated herein by reference as if recited in full herein. As used herein, the terms "hyperpolarize" and "polarize" are used interchangeably and mean to artificially enhance the polarization of certain noble gas nuclei over the natural or equilibrium levels. Such an increase is desirable because it allows stronger imaging signals corresponding to better MRI images of the substance in a targeted area of the body. As is known by those of skill in the art, hyperpolarization can be induced by spin-exchange with an optically pumped alkalimetal vapor or alternatively by metastability exchange. See U.S. Pat. No. 5,545,396 to Albert et al. The alkali metals capable of acting as spin exchange partners in optically pumped systems include any of the alkali metals. Preferred alkali metals for this hyperpolarization technique include Sodium-23, Potassium-39, Rubidium-85, Rubidium-87, and Cesium-133.

Alternatively, the noble gas may be hyperpolarized using metastability exchange. (See e.g., Schearer, L. D., *Phys Rev*, 180:83 (1969); Laloe, F., Nacher, P. J., Leduc, M., and Schearer L. D., AIP ConfProx #131 (Workshop on Polarized $^3$He Beams and Targets) (1984)). The technique of metastability exchange involves direct optical pumping of, for example, $^3$He without the need for an alkali metal intermediary. Since this process works best at low pressures (0–10 Torr), a compressor is typically used to compress the $^3$He after the hyperpolarization step.

Regardless of the hyperpolarization method used, once the active mechanism is no longer in effect, the polarization of the gas will inevitably decay toward its thermal equilibrium value, which is essentially zero. The present invention is configured to work with any hyperpolarization technique and, as will be appreciated by one of skill in the art, is not limited to working with any one type of machine, method, or particular gas.

Polarized Gas Relaxation Processes

Under most circumstances, the non-equilibrium polarization P(t) of a gas decays according to $$dP(t)/dt = -P(t)/T_1 \qquad 1.0$$

The overall decay rate is equal to the sum of rates from various mechanisms:

$$1/T_1 = (1/T_1)_{Gas} + (1/T_1)_{Surface} + (1/T_1)_{EMI} + (1/T_1)_{Gradient} \qquad 2.0$$

Gas Interaction Relaxation

The first decay term $+(1/T_1)_{Gas}$ represents the depolarization of the noble gas nuclei when interacting with each other and can also include interaction of the atoms with gaseous impurities such as oxygen. Thus, careful preparation of gas containment, transfer, and extraction systems is important for providing good polarization lifetimes as will be discussed further below. Examples of suitable gas extraction methods and apparatus are described in co-pending and co-assigned U.S. patent application Ser. No. 09/163,721, entitled "Hyperpolarized Noble Gas Extraction Methods, Masking Methods, and Associated Transport Containers," identified by Attorney Docket No. 5770-14, the disclosure of which is hereby incorporated by reference as if recited in full herein.

Even in the absence of all other relaxation mechanisms, collisions between identical polarized gas atoms impose a fundamental upper limit to the achievable $T_1$ lifetime. For example, $^3$He atoms relax through a dipole-dipole interaction during $^3$He—$^3$He collisions, while $^{129}$Xe atoms relax through N-I spin rotation interaction (where N is the molecular angular momentum and I designates nuclear spin rotation) during $^{129}$Xe—$^{129}$Xe collisions. In any event, because both processes occur during noble gas-noble gas collisions, both resulting relaxation rates are directly proportional to number density ($T_1$ is inversely proportional to number density). At one bar pressure, the theoretical maximum relaxation time $T_1$ of $^3$He is about 750 hours, and for $^{129}$Xe the corresponding relaxation time is about 56 hours. See Newbury et al., "Gaseous 3He—3He Magnetic Dipolar Spin Relaxation," 48 Phys. Rev. A., No. 6, p. 4411 (1993); Hunt et al., "Nuclear Magnetic Resonance of $^{129}$Xe in Natural Xenon," 130 Phys Rev. p. 2302 (1963).

Unfortunately, other relaxation processes such as surface relaxation, electromagnetic interference (EMI), and magnetic gradient relaxation can prevent the realization of these theoretical relaxation times. Accordingly, each of these mechanisms are of concern when handling hyperpolarized gases and are preferably addressed so as to allow for the overall relaxation time to be sufficiently large.

Surface-induced Relaxation

The $(1/T_1)_{Surface}$ term represents the surface-induced relaxation mechanism. For example, the collisions of gaseous $^{129}$Xe and $^3$He with container walls ("surface relaxation") have historically been thought to dominate most relaxation processes. For $^3$He, most of the known longer relaxation times have been achieved in special glass containers having a low permeability to helium. See Fitzsimmons et al., "Nature of surface induced spin relaxation of gaseous He-3," 179 Phys. Rev., No. 1, p. 156 (1969). U.S. Pat. No. 5,612,103 to Driehuys et al. describes using coatings to inhibit the surface-induced nuclear spin relaxation of hyperpolarized noble gases, especially $^{129}$Xe. The contents of this patent are hereby incorporated by reference as if recited in full herein. Similarly, co-pending and co-assigned U.S. patent application Ser. No. 09/126,448 to Deaton et al., and its related application identified by Attorney Docket No. 5770-12IP, describe preferred gas-contact surface materials and associated thicknesses, O-rings, and valve or seal materials and/or coatings which are friendly to the polarized state of the gas, i.e., which can inhibit surface/contact-induced relaxation mechanisms. The content of these applications are also hereby incorporated by reference as if recited in full herein.

Electromagnetic Interference

The relaxation mechanism expressed by the term $(1/T_1)_{EMI}$ is the relaxation induced by time-dependent electromagnetic fields. Indeed, EMI can potentially destroy the hyperpolarized state of the gas (EMI is particularly problematic if coherent at the magnetic resonance frequency). Unfortunately, EMI can be generated by relatively common sources, For example, EMI is typically generated from a vehicle's engine, high voltage lines, power stations and other current carrying entities. As such, transport away from the hyperpolarized gas production site can expose the hyperpolarized gas to these undesirable relaxation sources that, in turn, can dramatically reduce the polarization lifetime of the transported gas.

Fluctuating fields are particularly deleterious if they are coherent at the magnetic resonance frequency. For example, assuming a generally worst case scenario of a highly coherent oscillating field, it is expected that the relaxation rate is comparable to the Rabi frequency:

$$(1/T_1)_{EMI} \approx \gamma H_{AC}/2 \qquad 2.10$$

Here, "$\gamma$" is the gyromagnetic ratio of the spins, and "$H_{AC}$" is the magnitude of the transverse fluctuating field. A resonant field $H_{AC}$ of only $1\mu G$ would cause relaxation on a time scale of order 100 seconds for $^3$He. On the other hand, if the field is randomly fluctuating, the relaxation rate is given by $$(1/T_1)_{EMI} = \gamma^2 <H_{AC}^2> \tau_c/(1+\omega^2\tau_c^2) \qquad 2.20$$

where "$\tau_c$" is the autocorrelation time of the fluctuations, "$\omega$" is the Larmor frequency of the spins, and "$<H_{AC}^2>$" is the mean value of the square of the fluctuating transverse field component. In the random fluctuation case, the rate can be suppressed by increasing $\omega$, (which is proportional to the holding field strength), particularly if $\omega\tau_c>1$. In either case, the relaxation rate can be suppressed by reducing the magnitude of the interference $H_{AC}$.

Magnetic Field Gradients

Magnetic gradient relaxation expressed by the term $(1/T_1)_{Gradient}$ is associated with the relaxation attributed to the exposure of the hyperpolarized noble gases to inhomogeneous static magnetic fields. Generally stated, as the polarized gas atoms diffuse or move through an inhomogeneous magnetic field, they experience a time-dependent field, which can introduce depolarizing activity onto the hyperpolarized atoms. For example, at typical pressures (i.e., about 1 bar), the relaxation rate attributed to a static magnetic field gradient can be expressed by the following equation:

$$(1/T_1)_{Gradient} = D(|\nabla B_x|^2 + |\nabla B_y|^2)/B_z^2 \qquad 2.30$$

Here, "$B_z$" is the primary component of the static magnetic field, "$\nabla B_x$" and "$\nabla B_y$" represent the gradients of the transverse field components, and "D" is the diffusion coefficient of the polarized atoms through the gas. For example, for pure $^3$He at 1 bar pressure, the diffusion coefficient $D \approx 1.9$ cm$^2$/s. In the earth's magnetic field (generally represented by a static magnetic field of about 0.5 G), a 5 mG/cm transverse field gradient causes a relaxation rate $(1/T_1)_{Gradient}$ of about $1.9 \times 10^{-4}$ s$^{-1}$ (i.e., a $^3$He $T_1$ of about 1.5 hours). In contrast, in a 5 gauss field (as opposed to a 0.5 gauss field), the same 5 mG/cm gradient will typically yield a $T_1$ of about 150 hours. Thus a magnetic field homogeneity on the order of $10^{-3}$ cm$^{-1}$ is desirable to make gradient relaxation tolerable at these pressures. Alternatively, higher gradients are acceptable if the $^3$He is pressurized to at least several bars of pressure, or alternatively mixed with another gas such as nitrogen or argon to restrict diffusion, i.e., lower the diffusion coefficient. As will be appreciated by those of skill in the art, during transport, it is desirable to avoid inhomogeneous magnetic fields, e.g., to avoid nearby ferromagnetic objects. For example, it is desired to maximize to the extent possible the spatial distance between the hyperpolarized gas and objects that can produce strong magnetic fields and/or magnetic field gradients.

Shielding

The present invention recognizes that unless special precautions are taken, relaxation due to external magnetic fields (static and/or time dependent) can dominate all other relaxation mechanisms. As discussed above, both gradients in the static field and (low frequency) oscillating magnetic fields experienced by the hyperpolarized gas can cause significant relaxation.

Advantageously, the instant invention employs an (externally) applied substantially static magnetic holding field "$B_H$" to substantially protect the hyperpolarized gas from depolarizing effects attributed to one or more of the EMI and gradient fields during transport. The instant invention employs a magnetic holding field which raises the Larmor frequency of the hyperpolarized gas above the region of noise (1/f), i.e., the region where the intensity of ambient electromagnetic noise is typically high (this noise is typically under about 5 kHz). Further, the magnetic holding field of the instant invention is also preferably selected such that it raises the frequency of the hyperpolarized gas to a level which is above those frequencies associated with large acoustic vibrations (these acoustic vibrations are typically less than about 20 kHz). As will be discussed below, the increased frequency associated with the applied magnetic holding field advantageously allows a transport unit to have greater electromagnetic shielding effectiveness for a given housing thickness (the housing used to hold the hyperpolarized gas therein during transport). The skin depth "$\delta$" of a conductive shielding material is inversely proportional to the square root of the frequency. Thus, at 25 kHz, an exemplary skin depth for aluminum is about 0.5 mm, as compared to about 2.0 mm at 1.6 kHz.

Preferably, the magnitude of the magnetic holding field of the instant invention is selected so that any external field-related fluctuations are small in magnitude compared to the field strength of the holding field; in this way the holding field can minimize the hyperpolarized gas's response to unpredictable external static field gradient-induced relaxation. This can be accomplished by applying to the hyperpolarized gas a proximately positioned magnetic holding field which is sufficiently strong and homogeneous so that it minimizes the unpredictable static field-related relaxation during transport. A sufficiently homogeneous holding field preferably includes (but is not limited to) a magnetic holding field which has homogeneity which is on the order of about at least $10^{-3}$ cm$^{-1}$ over the central part of the holding field. In the previous example, if a homogeneous field of about 10 G were applied, the same 5 mG cm$^{-1}$ gradient would instead result in $T_1 \approx 600$ hr. More preferably, the magnetic holding field homogeneity is about at least $5 \times 10^{-4}$ cm$^{-1}$ over about a region of interest (i.e., the region of interest is region associated with the major volume of the hyperpolarized gas in the container(s)) in the transport unit. Preferably this volume is sized and configured as a volume in space representing about at least a three-inch diameter sphere. Further, the transport unit 10 of the instant invention includes and provides a magnetic holding field which is positioned, sized, and configured relative to the hyperpolarized gas held therein such that it also minimizes the EMI or oscillating magnetic field depolarization effects on same. The depolarizing effect of EMI is preferably (substantially) blocked by applying the magnetic holding field ($B_H$) proximate to the gas so that the resonant frequency of the hyperpolarized gas is adjusted to a predetermined frequency. Preferably, the predetermined frequency is selected such that it is above or outside the bandwidth of prevalent time-dependent fields produced by electrically powered or supplied sources.

Alternatively, or additionally, the external interference can be shielded by positioning a substantially continuous shield or shipping container having at least one layer formed of a conductive material, such as metal, around the hyperpolarized gas in the container. The preferred shielding thickness is related to the spatial decay constant of an electromagnetic wave or skin depth "$\delta$". The skin depth $\delta$ at an angular frequency "$\omega$", given by "$\delta = c/(2\pi\mu\sigma\omega)^{1/2}$", where "$\mu$" is the magnetic permeability and "$\sigma$" is the electrical conductivity of the material. At these frequencies, the Larmor radiation wavelength is relatively long (~10 km), and is much larger than the container size. The shielding effectiveness is therefore dependent upon the container geometry as well as the shielding thickness. For a thin spherical conductor of radius "a" and thickness "t", the shielding factor for wavelengths "$\lambda$" where $\lambda \gg a$ can be approximately represented by the following equation $$F = (1 + (2at/3\delta^2)^2)^{1/2} \qquad 2.4$$

Interestingly, the shielding effectiveness increases as the size (radius) of the shield is increased. It is therefore preferred that the metallic enclosure used to shield or surround the hyperpolarized gas be configured and sized to define an internal volume and spatial separation relative to the gas which is sufficient to provide increased shielding effectiveness. Stated differently, it is preferred that the opposing walls of the enclosure are spaced apart a predetermined distance relative to the position of the gas container held therein. Preferably, the walls define a minimum linear separation for the major volume of the container or chamber (the portion holding a major portion of the hyperpolarized gas or product) such that there is about at least 1.5 inches, and more preferably at least about 2.0 inches, and even more preferably at least about 2.5 inches of distance between the metallic wall and the leading edge of the gas holding chamber on all sides.

As shown in FIG. 1, the transport unit 10 has an enclosure 60 with a geometry in which the walls of the enclosure are configured and sized to provide an internal volume 65 or geometry which is relatively large in comparison to the size of the gas container(s) 30 (30b, FIG. 12). As is also shown, the walls 63A, 63B, 63C, 63D are configured such that the gas holding chamber 30, when in position in the enclosure 60, is spaced apart a distance from the adjacent wall segments to provide sufficient spacing to facilitate the shielding effectiveness of the metallic wall. That is, the opposing walls 63B, 63C and 63A, 63D (and preferably including the opposing top and bottom walls 63E, 60A) each have a minimum separation distance of preferably at least about 1.5 inches, and more preferably at least 2.0 inches, and still more preferably at least about 2.5 inches in all directions from the major portion of the gas holding chamber 30. In a preferred configuration, the separation distances of the container 30 (30b, FIG. 12) as held in the transport unit 10, is sized and geometrically configured to define a maximum separation ratio. That is, the separation ratio can be described as the linear distance from the center of the major volume of the container holding a volume of hyperpolarized gas to the edge thereof (i.e., the linear half width, or the radius of a spherical gas chamber) to the minimum linear separation distance of each (or the closest) wall from the leading edge of the portion of the gas holding chamber holding the major volume of the gas. Preferably, the container and enclosure are configured to provide a ratio which is less than about 0.60.

Alternatively, or additionally, the transport unit 10 can be configured with at least one layer formed from about 0.5 mm thick of magnetically permeable material, such as ultra low carbon steel soft iron, or mu-metals (by virtue of their greater magnetic permeability). However, these materials may significantly influence the static magnetic field and must be designed accordingly not to affect the homogeneity adversely.

Irrespective of the skin depth of the materials (types of materials and number of layers) used to form the shipping container enclosure, application of a homogeneous magnetic holding field proximate to the hyperpolarized gas can help minimize the gas depolarization by virtue of decreasing the skin depth $\delta$, which is inversely proportional to the square root of the frequency. Further, it helps by pushing the resonant frequency of the gas outside the bandwidth of common AC fields. It is preferred that the resonant frequency of the hyperpolarized gas be raised such that it is above about 10 kHz, and more preferably be raised such that it is between about 20–30 kHz. Stated differently, it is preferred that for shielding, the applied magnetic holding field have a field strength of about 2 to 35 gauss. It is more preferred that for $^{129}Xe$, the magnetic holding field is preferably at least about 20 Gauss; and for $^3He$, the magnetic holding field is preferably at least about 7 Gauss.

Transport Unit

Referring now to FIG. 1, a transport unit 10 is illustrated according to a preferred embodiment of the instant invention. As shown, the transport unit 10 includes a magnetic field generator 20' disposed therein, which provides a magnetic holding field ($B_H$) for the gas. As shown, the magnetic field generator is a solenoid 20, which is configured and sized to receive a hyperpolarized gas storage chamber 30 therein. The transport unit 10 also includes a power source 40 and operating circuitry 50 preferably provided on an internally disposed printed circuit board 51. The transport unit 10 preferably includes a substantially non-ferromagnetic metallic case or housing enclosure 60 having a predetermined skin depth appropriately sized to provide desired shielding, and which includes a bottom portion 60B and a top 61A (FIG. 5) that open to facilitate easy access to the exit port 31 and valve 32 of the gas chamber 30. It is preferred that the transport unit 10 be configured with a minimal amount of ferromagnetic materials on or inside the transport unit 10 (i.e., is substantially free of ferromagnetic materials that are not intended for creating the homogeneous holding field). Although for ease of discussion, the term "transport" is used to describe the unit, it will be appreciated by one of skill in the art, that the instant invention may also be used to store a quantity of hyperpolarized gas product therein. As such, the term "transport unit" includes a unit that can be used as either a storage unit, a transport unit, or both a storage and transport unit.

Figure 5:
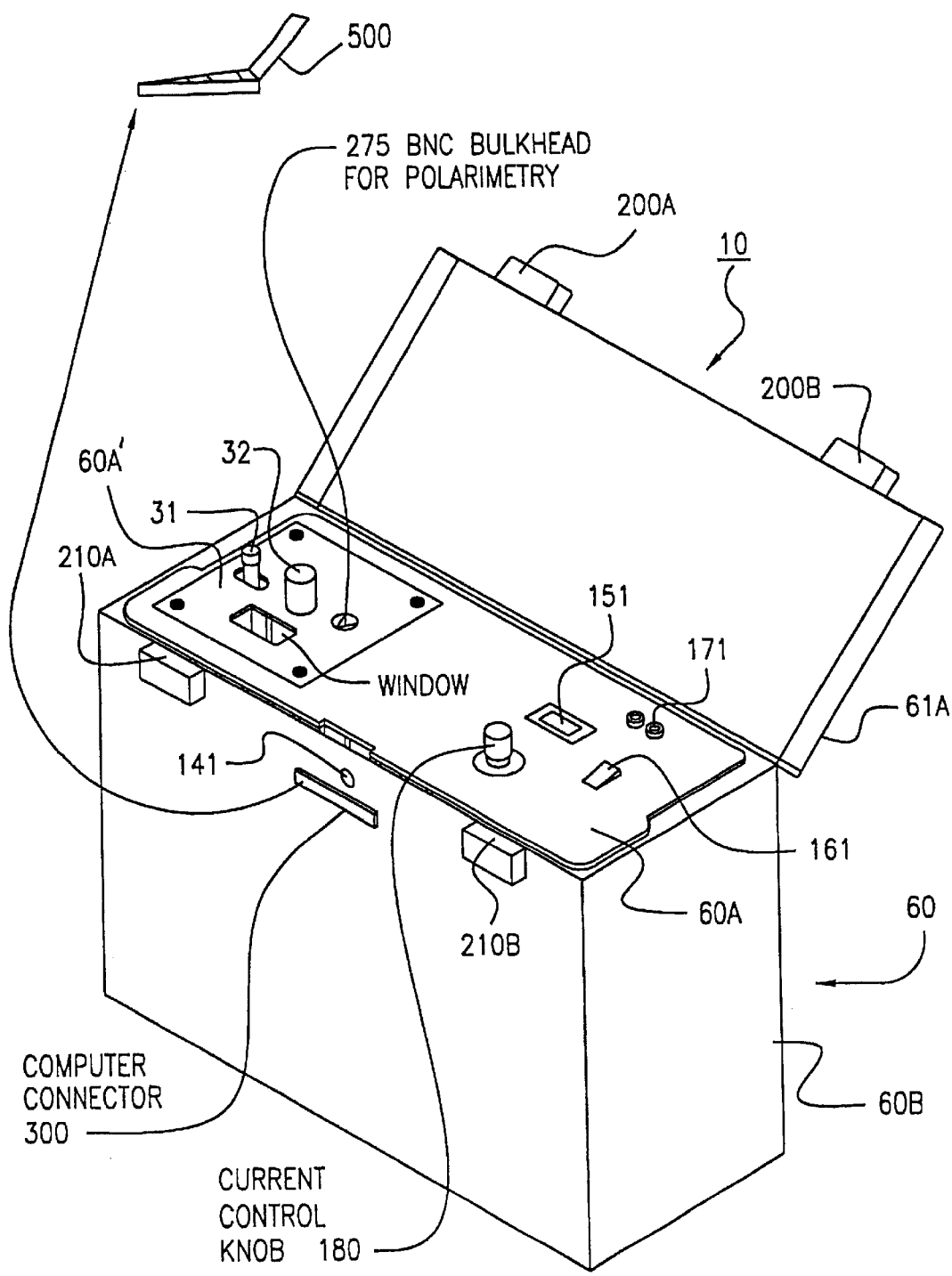
FIG. 5 is a front perspective view of the transport unit shown in FIG. 1.

As shown in FIGS. 1 and 5, the top 61A of the housing is hinged to the bottom of the case 60B, which defines an enclosure volume 65. Preferably, as shown in FIG. 1, the enclosure volume 65 is defined by a contiguous arrangement of four upstanding sidewalls 63A–63D (63D not shown) connected by a bottom wall 63E and a top face-plate 60A, 60A'. Thus, the enclosure 65 surrounds the gas chamber 30 and other internally mounted components (such as a power source 40 and operating circuitry 50).

As shown in FIG. 5, the top portion 61A preferably includes latches 200A, 200B which engage with corresponding components 210A, 210B positioned on the outside wall of the bottom portion of the case 60B to secure the top 61A to the bottom to the bottom 60B when the top 61A is closed (i.e., preferably during transport). Preferably, the enclosure 60 and, indeed, the entire transport unit 10, is configured to be polarization-friendly (substantially devoid of paramagnetic and ferromagnetic materials) such that the transport unit 10 does not introduce significant reductions in the polarization level of the hyperpolarized gas therein.

Generally stated, as electromagnetic leakage is proportional to holes or openings in the housing 60, it is preferred, either when the top of the housing 61A is closed or by configuring the face plate 60A to attach to the bottom of the case 60B such that the exterior walls of the housing 60 define a substantially continuous body (without openings) to minimize the entry of electromagnetic waves inside the housing 60. Of course, the housing 60 can include apertures as long as they are positioned or formed on the housing 60 such that any electromagnetic interference leakage is directed away from the solenoid core 33 where the gas chamber 30 resides and/or are configured with a protective covering or seal to provide sufficient housing integrity to minimize polarization loss attributed thereto. One suitable housing 60 is a relatively compact aluminum case (having about a 1 mm wall thickness) manufactured by Zero Enclosures of Salt Lake City, Utah and was modified to substantially remove ferromagnetic hardware.

Preferably, the bottom of the case 60B and the face plate 60A and/or top 61A includes at least one layer of an electrically conducting metal thereon, having a sufficient skin depth to thereby provide one or more of shielding from external electromagnetic radiation, physical protection, and support of the gas container during transport. Alternatively, or additionally, the components of the housing 60 which define the enclosure 65 (such as the walls and bottom 63A–63D, 63E and top 61A) include at least one layer of magnetically permeable material to provide either additional electromagnetic shielding, DC magnetic shielding, and/or a flux return.

Preferably, as shown in FIG. 1, the transport unit 10 also comprises a metal face plate 60A, 60A' positioned over the opening defined by the upper surface of the case when the top 61A is opened. As shown in FIGS. 1 and 5, the face plate 60A, 60A' is configured to substantially enclose the side walls and bottom of the housing to provide an enclosure for the solenoid 20 when the top 61A is open and yet also configured to allow a user access to a polarized gas chamber valve 32 and the hyperpolarized gas exit port 31.

In a preferred embodiment, after delivery to a desired location, the valve 32 is opened and the hyperpolarized gas is released from the gas chamber 30 through the exit port 31 while the gas chamber 30 itself remains captured in the substantially enclosed housing 60. The bottom housing 60 can add extra protection to personnel in the gas release area because the housing 60 surrounds a substantial portion of the gas chamber 30 therein, thereby providing a physical shield from any unplanned release or untimely breakage of the chamber itself (typically comprising an alumnosilicate glass) and which is typically transported under pressure. Further details of the preferred gas chamber 30 will be discussed below.

Solenoid

Figure 2:
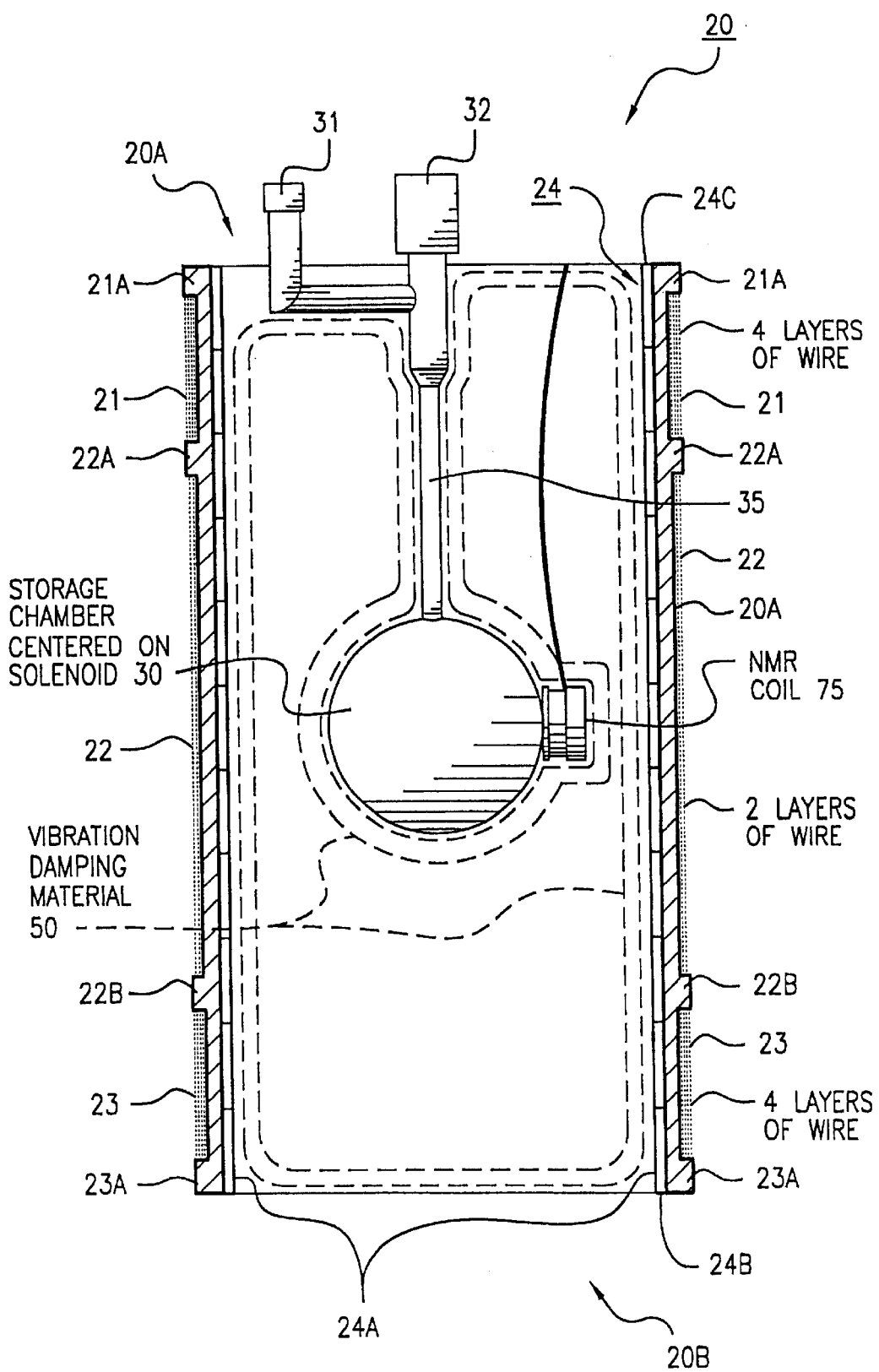
FIG. 2 is an enlarged cutaway front view of the solenoid and gas chamber shown in FIG. 1.

Turning to FIG. 2, it is preferred that the transport unit comprise an electromagnet for providing the magnetic holding field. FIG. 2 illustrates a preferred embodiment of the electromagnet configured as a solenoid 20 comprises a plurality of electrical coil segments for generating a substantially homogeneous static applied magnetic holding field ($B_H$). Of course, other electrical wire configurations (i.e., electromagnetic arrangements) can also be used as will be appreciated by one of skill in the art. As will also be appreciated by one of skill in the art, other magnetic field generators can also be employed such as permanent magnets (so long as they provide sufficient homogeneity). Preferably, the solenoid 20 comprises at least three (3) electrical coil segments 21, 22, 23 which are wrapped around an outer surface of the cylindrical wall of the solenoid body or core 20A. During fabrication, this outer surface placement of the coil segments 21, 22, 23 allows the outer wall of the solenoid core 20A to act as the wrapping spool. The cylindrical spool can be formed of various preferably non-conducting materials such as polyvinyl chloride (PVC). Of course, the coil segments 21, 22, 23 can be alternatively positioned on the cylindrical body. For example, the coil segments 21, 22, 23 can be wrapped onto an intermediate layer of a cylindrical body (or even an inner layer) as will be appreciated by those of skill in the art.

Figure 3:
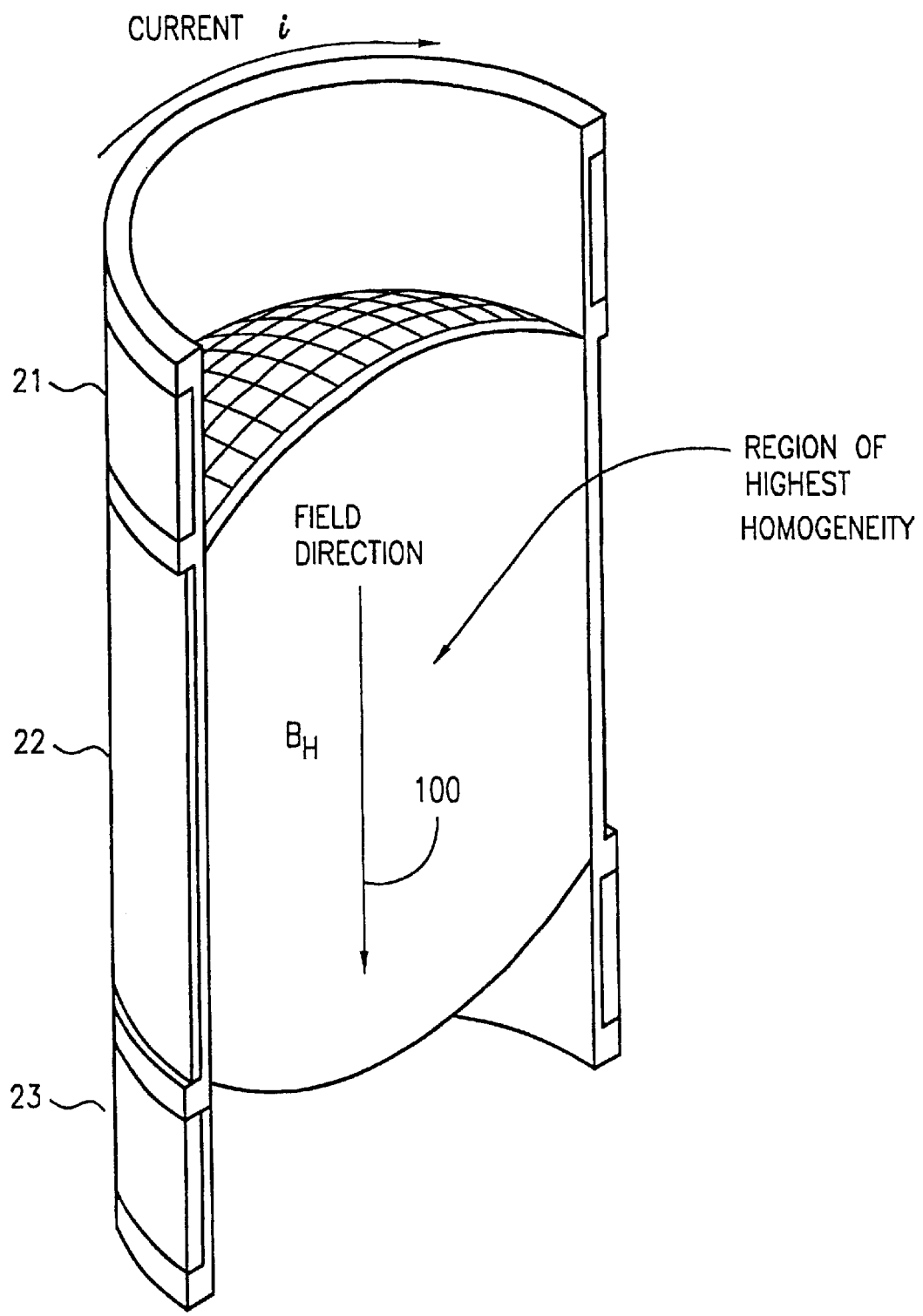
FIG. 3 is a cutaway perspective view of the solenoid of FIG. 2A illustrating the current direction and the magnetic holding field direction and the region of highest homogeneity in the solenoid.

As shown in FIGS. 1, 2 and 3, the solenoid 20 is oriented such that it extends longitudinally from the opposing top and bottom ends of the transport unit 10. The coil segments 21, 22, 23 are circumferentially wrapped around the respective portions of the cylindrical wall of the solenoid core 20a and are preferably configured such that the magnetic holding field $B_H$ (FIG. 3) is directed downward such that it preferably aligns with the predominant direction of the earth's magnetic field (the field direction is generally indicated by element 100). As such, the current in the solenoid coil segments 21, 22, 23 is directed clockwise when viewing the solenoid from the top. This earthly directional alignment can maximize the magnitude of the holding field with a given current.

Figure 2A:
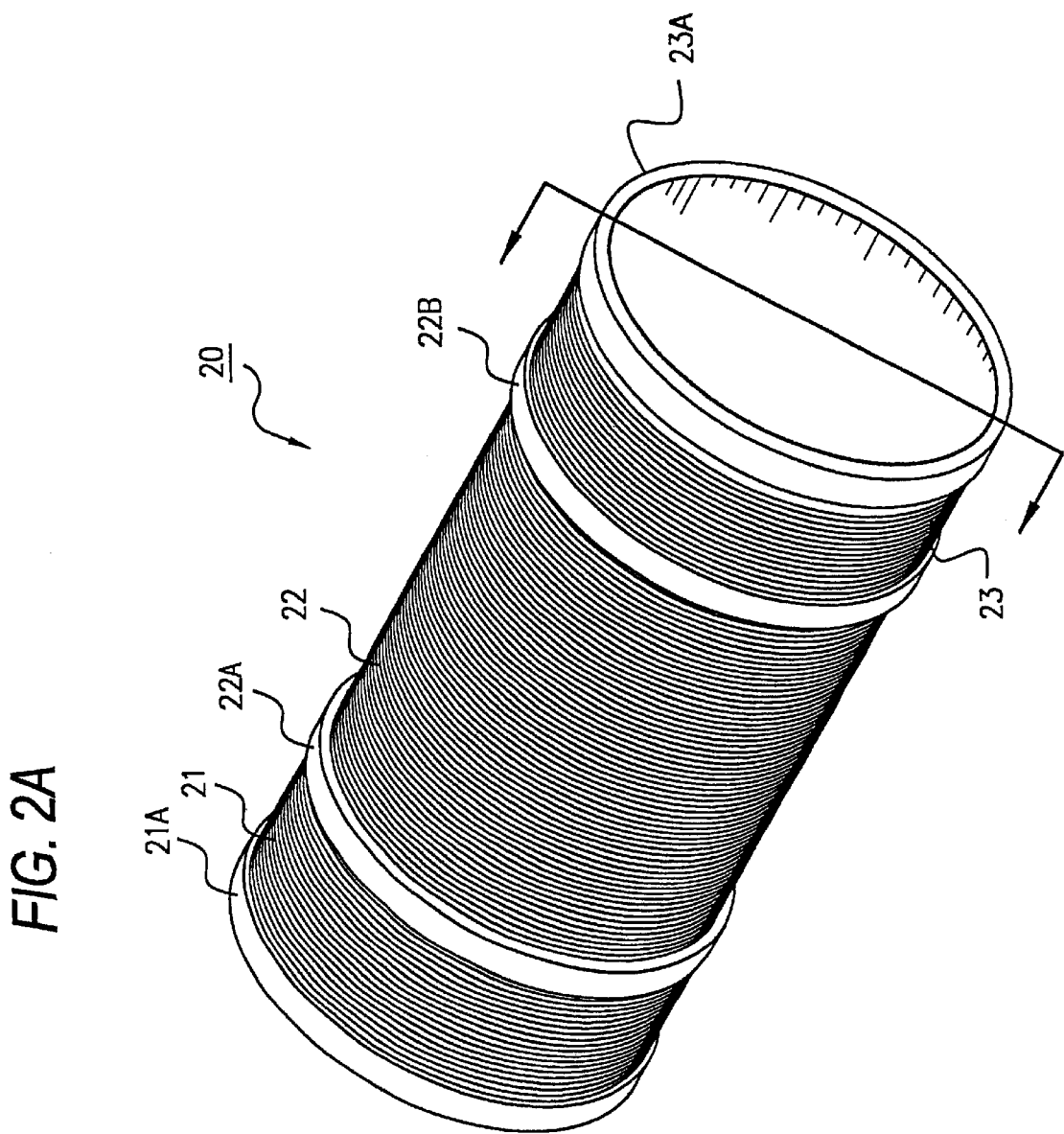
FIG. 2A is a perspective view of the solenoid shown in FIGS. 1 and 2.

As shown in FIGS. 2 and 2A, the first and third coil segments 21, 23 are preferably positioned proximate to the top and bottom 20A, 20B of the solenoid, respectively. The second coil segment 22 is positioned intermediate the first and third coil segments 21, 23. As shown, the second segment 22 is spatially separated by a separation distance 22A, 22B from the first and third coil segments 21, 23.

FIG. 1 shows a preferred embodiment wherein substantially the entire inner diameter of the solenoid 20 is covered with a thin conductive material layer such as a metallic film or tape 24. FIGS. 1 and 2 illustrate that the thin metallic layer 24 acts to provide a separate columnated electrical shield 24a which extends between the top plate 60A and the top surface of the bottom of the case 63E. As shown, the shield 24a is formed as a thin metallic layer 24 which is arranged as a series of wrapped and overlapping layers of aluminum foil tape which extends from the top to the bottom of the solenoid 20. This thin metallic layer 24 can also be provided by other metallic finishes, such as by a metallic coating, metallic film or metallic elastomer and the like.

Preferably the shield 24a is configured such that at least the bottom end 24b of the shield is in electrical contact with the case 60. In a preferred embodiment, the bottom end 24b is configured to be in electrical contact either directly or indirectly (i.e., via other conductive components) with the case. In this embodiment, the bottom end 24b is configured such that the end defines a continuous electrical connection around the entire bottom edge 24b. Of course, other components can be used to define an electrical bridge between the shield 24a and the case.

In another embodiment, both the top edge 24c and the bottom edge 24b of the shield 24a are arranged to define a continuous electrical contact with the respective adjacent portions of the case 60.

Figure 3A:
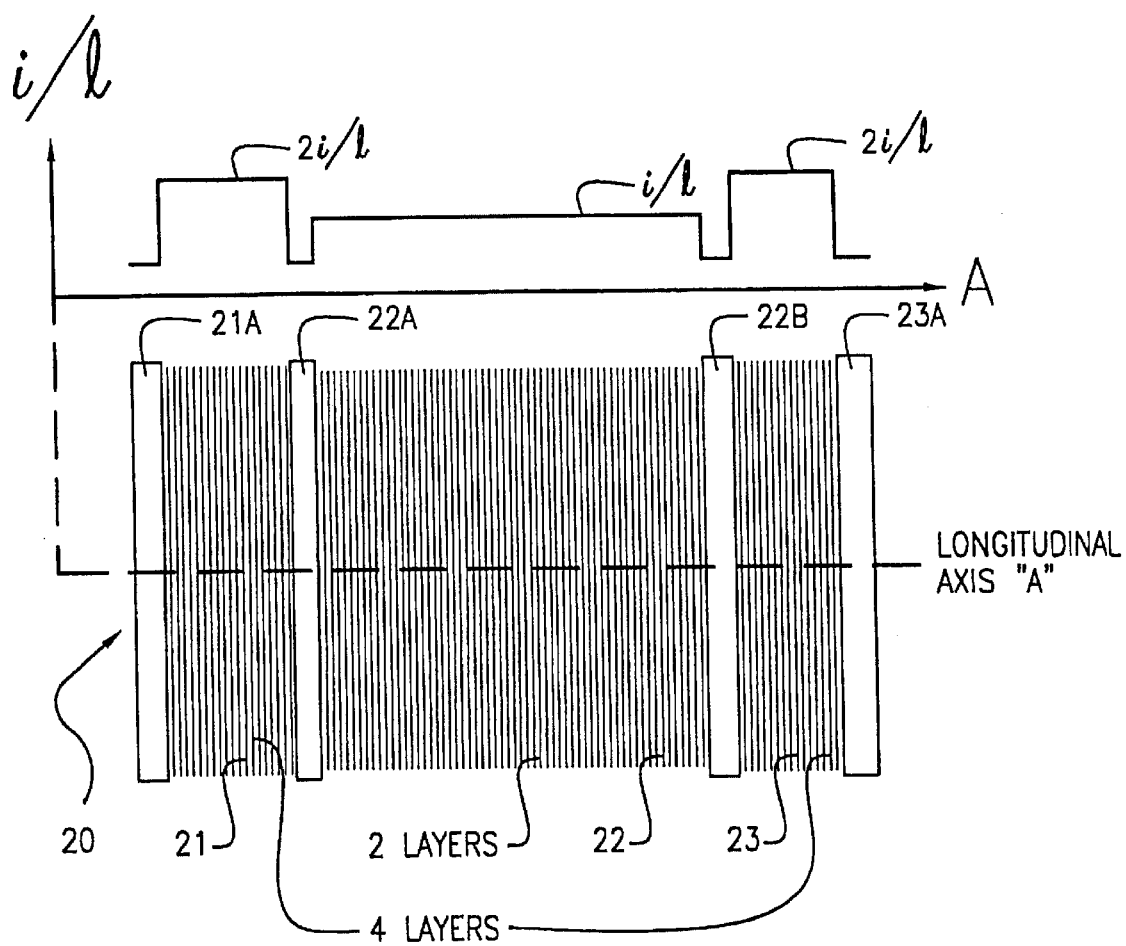
FIG. 3A is a graph that illustrates a preferred winding/current distribution relative to the distance along the length of the solenoid, with (2$i$) representing a current density which is twice that of the center coil segment ($i$), along with points of negligible current between the coil segments.
Figure 10:
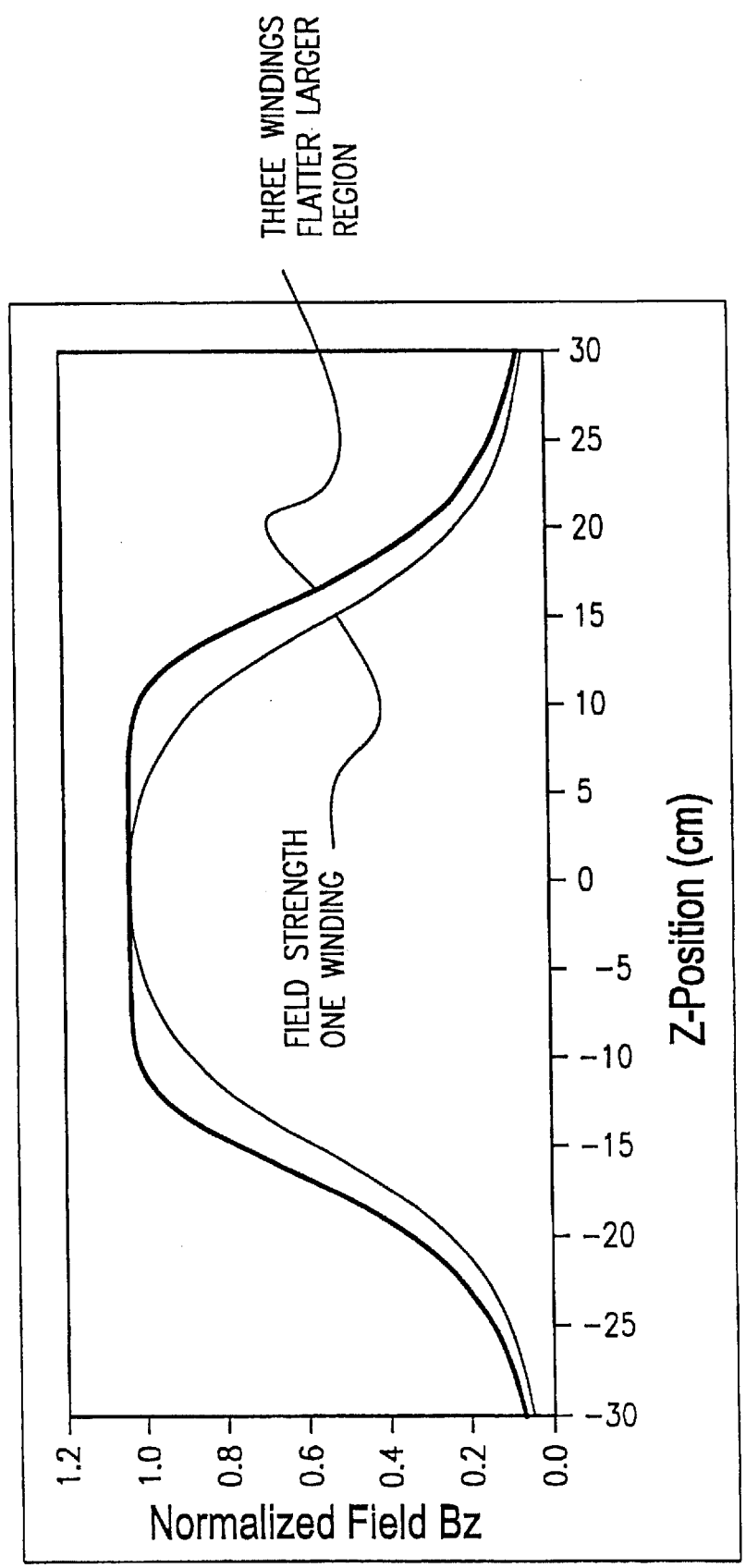
FIG. 10 is a graphical representation of the normalized magnetic field generated by an embodiment of the solenoid of the instant invention (top bell-shaped curve) compared to a coil having uniform current density per unit length (bottom bell-shape curve).

Further, in a preferred embodiment, as illustrated in FIG. 3A, the first and third coil segments 21, 23 are configured with an increased number of wire layers relative to the second coil segment 22. A preferred current distribution is also illustrated in FIG. 3A. The increased number of layers associated with the first and third coil segments 21, 23 relative to the second coil segment 22 acts to provide additional current density in these segments and to enlarge the homogeneous region, as shown in FIG. 3. FIG. 10 illustrates a broader "flatter" field strength (Bz) which a solenoid having a plurality of winding segments can provide relative to a single winding configuration of the same length having a uniform current density. FIG. 10 illustrates the single winding field as the bottom "bell-shaped" graph. As such, a solenoid with a plurality of winding segments can increase the homogeneous holding region in the solenoid along a greater distance about the center of the solenoid body (distance from "0" along the "z-position").

As shown in FIG. 3A, the solenoid 20 is turned on its side (relative to the transit position shown in FIG. 1) and a preferred current distribution relative to each coil segment 21, 22, 23 is graphically illustrated. The first and third coil segments 21, 23 correspond to a first current density value ($2i/l$) and the intermediate or second coil segment corresponds to a lesser current density value, preferably about half the end current density value (i.e., about ($i/l$)). (There is negligible current in the gaps 21A, 22A, 22B and 23A). As shown, it is preferred that each of the first and third coil segments 21, 23 have a current density value which is substantially the same, while the second coil segment 22 has a current density value ($i/l$) which is about half of that of the first and third coil segments 21, 23. As noted above, the additional current density is preferably provided by additional numbers of wire layers in the first and third coil segments 21, 23.

Preferably, the first and third coil segments 21, 23 are configured with a predetermined number of wire layers that extend about a first and third solenoid longitudinal distance. The second segment 22 is configured with about half of the number of wire layers relative to the first and third coil segments 21, 23 and extends about a longer second solenoid longitudinal distance. Also, as illustrated in FIG. 3A, preferably the first and third coil segments 21, 23 include about four wire wrap layers (wire is wrapped in four layers in these segments, one layer on top of the other), each having about a 2.0 inch length, while the second segment 22 includes about two wire wrap layers having about a 7.0 inch length. The solenoid 20 preferably is sized to provide about a 6.0 inch inner diameter. These dimensions are particularly suitable for a single dose quantity of hyperpolarized gas that is held in a 3 inch diameter spherical gas chamber 30 having a capillary stem 35 as shown in FIG. 1. This gas chamber 30 and solenoid 20 configuration provides about a 1.5 inch radial separation between the solenoid inner diameter and the gas chamber outer diameter. Of course, other solenoid 20 dimensions and coil segment configurations (lengths, numbers of layers etc., and/or permanent magnet arrangements) can be used for alternatively sized and shaped containers 30.

In its preferred operative position, as shown in FIGS. 1 and 2, the gas chamber 30 is preferably disposed in the solenoid 20 such that the spherical or major portion 33 of the gas chamber 30 is positioned the area of increased homogeneity within the solenoid 20 (e.g., the center of the solenoid 20 and/or the center of the second coil segment 22). The positioning can be secured by suspending the gas chamber 30 from the top plate 60A' (FIG. 1) or by positioning a non-conducting gas friendly platform or base or the like under the gas chamber 30 (not shown). Preferably, as shown in dotted line in FIG. 2, the gas chamber 30 is disposed in the solenoid 20 such that it rests on hyperpolarized gas friendly packaging which acts as vibration damping material 50 to help insulate the gas chamber 30 from undue exposure to vibration during transport. Also as shown, the packing material 50 extends securely and snugly around and about the capillary stem 35 to help cushion and insulate the container during shipment. In any event, it is preferred that the gas chamber 30 be well supported in the high homogeneity region, as the magnetic holding field's homogeneity is spatially determined (spatially variable) and translation of the gas chamber 30 thereabout can result in the hyperpolarized gas being potentially exposed to an inhomogeneous region, thereby potentially reducing the polarized life of the hyperpolarized gas product.

In any event, it is preferred that the coil segment configuration is such that each of the first and third coil segments 21, 23 provides an increased current density relative to the second or intermediate coil segment 22. In this configuration, the solenoid electrical coil segments 21, 22, 23 are sized and configured with respect to the solenoid volume to provide adequate magnetic field homogeneity over a larger central volume and advantageously do so in a relatively compact manner relative to previous coil designs. Preferably, the three coils 21, 22, 23 are electrically connected in series and, as such, the end coil segments are electrically connected to the power source 40 (FIG. 1). Of course, the current can alternatively be separately provided or otherwise electrically supplied to the coil segments 21, 22, 23. For example, as will be appreciated by those of skill in the art, a separate battery and associated circuitry (not shown) can supply the second coil 22 while a first battery is used to power the first and third coils 21, 23.

In a preferred embodiment, the first and third coil segments have about 198 windings while the second or central coil segment includes about 347 windings (i.e., the second coil segment 22 preferably has above about 1.5 times the number of windings of the first and third coil segments 21, 23). Thus, in a preferred embodiment, the solenoid 20 is configured with about 743 windings thereon. For this configuration the ratio of field strength to current is about 23.059 G/A. Thus, the field strength at 300 mA is about 6.918 gauss and the field strength at 320 mA is about 7.379 gauss. A suitable wire is 18 gauge HML from MWS Wire Industries, Westlake Village, Calif.

Preferably, for transit purposes, the transport unit power source 40 is a 12V DC battery (such as those used to power motorcycles). However, at docking stations or an end-use site, the transport unit 10 can be conveniently plugged into an exterior power source to bypass and preserve the battery charge. Also the transport unit power source 40 is configured via operating circuitry 50 to provide an adjustable current supply to the solenoid 20 of about 100 mA to about 2.0A. Thus, the solenoid 20 is preferably configured to provide a magnetic holding field of between about 2 to 40 gauss. The operating circuitry 50 of the transport unit 10 will be discussed further below.

Gas Chamber

Figure 12A:
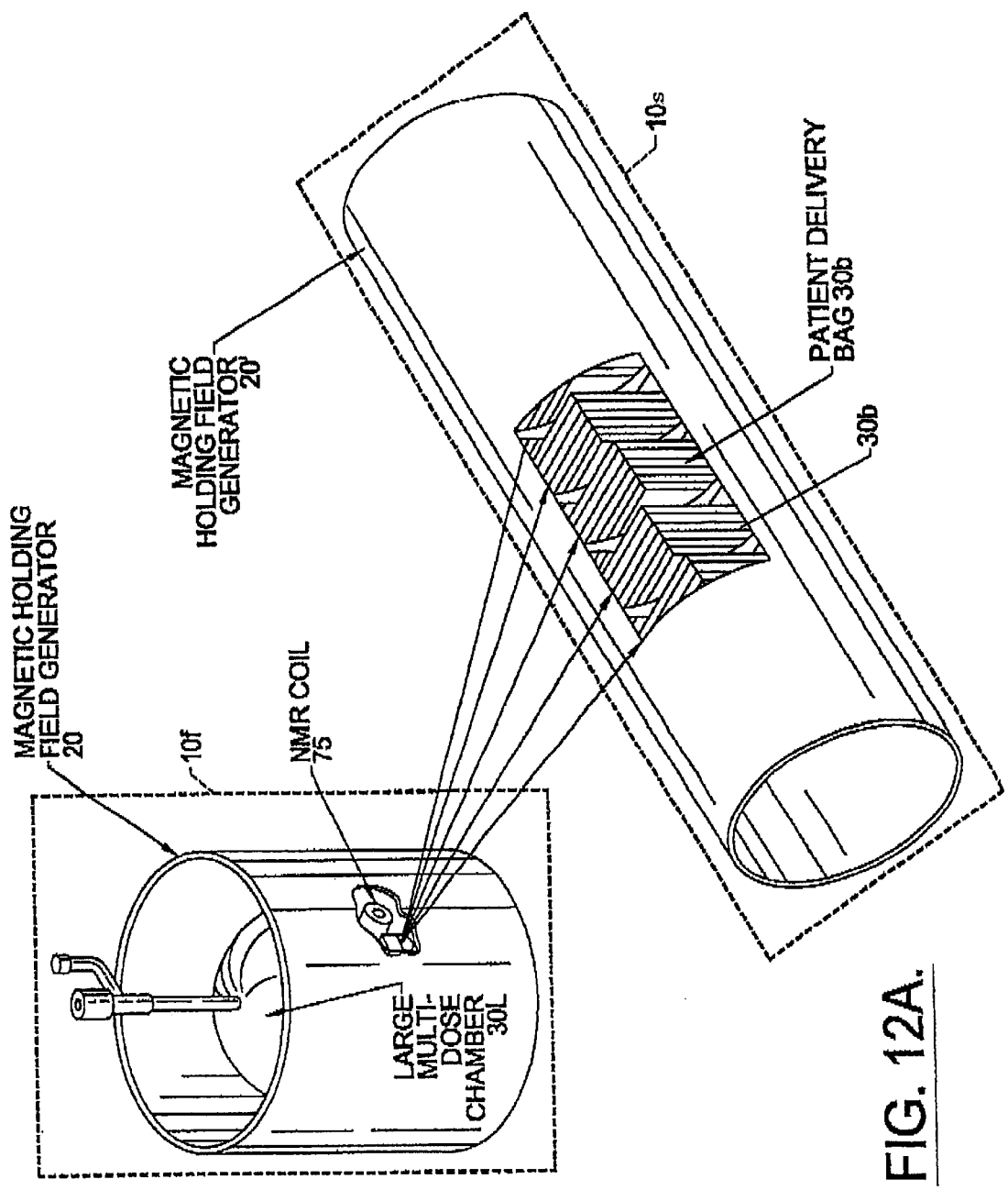
FIG. 12A is a perspective partial cutaway view of a multi-transport distribution system. The distribution system delivers a multi-dose container to a second site remote from the polarization site. At the second site, the hyperpolarized product in the multi-dose container is divided, mixed, or otherwise formulated into resilient single use containers for delivery to a teritary (preferably clinical use site) according to the present invention.
Figure 12B:
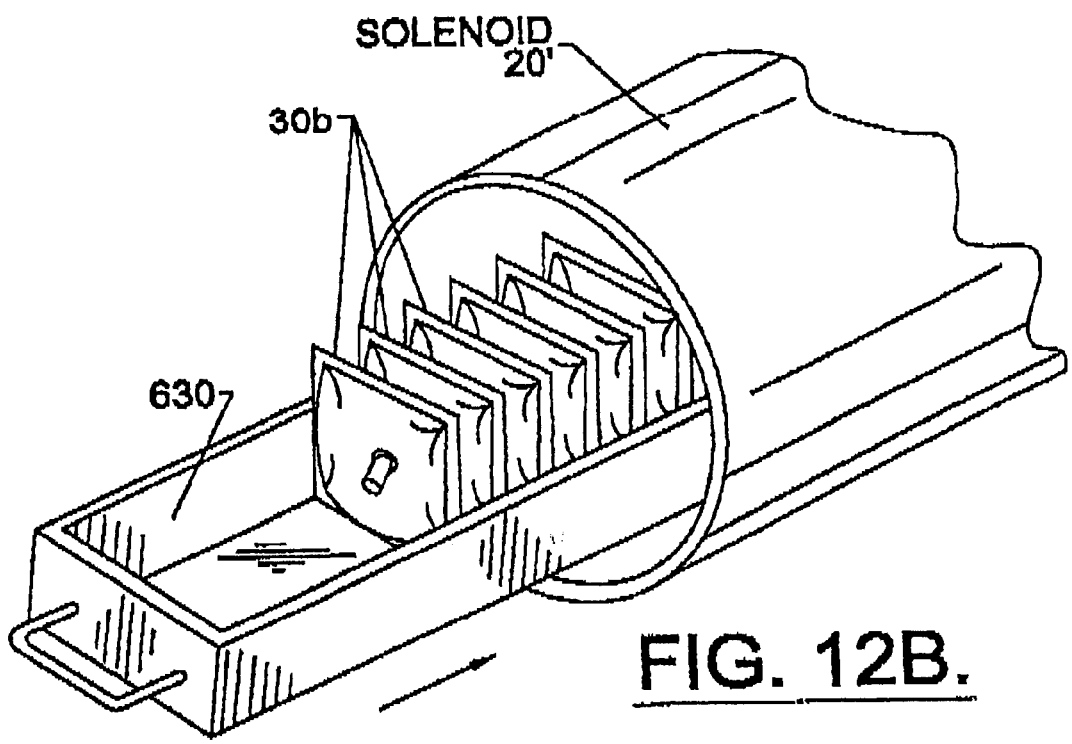
FIG. 12B is an exploded view of a tray for facilitating positioning of a plurality of single-sized resilient containers in a single solenoid sized to accommodate same.
Figure 13:
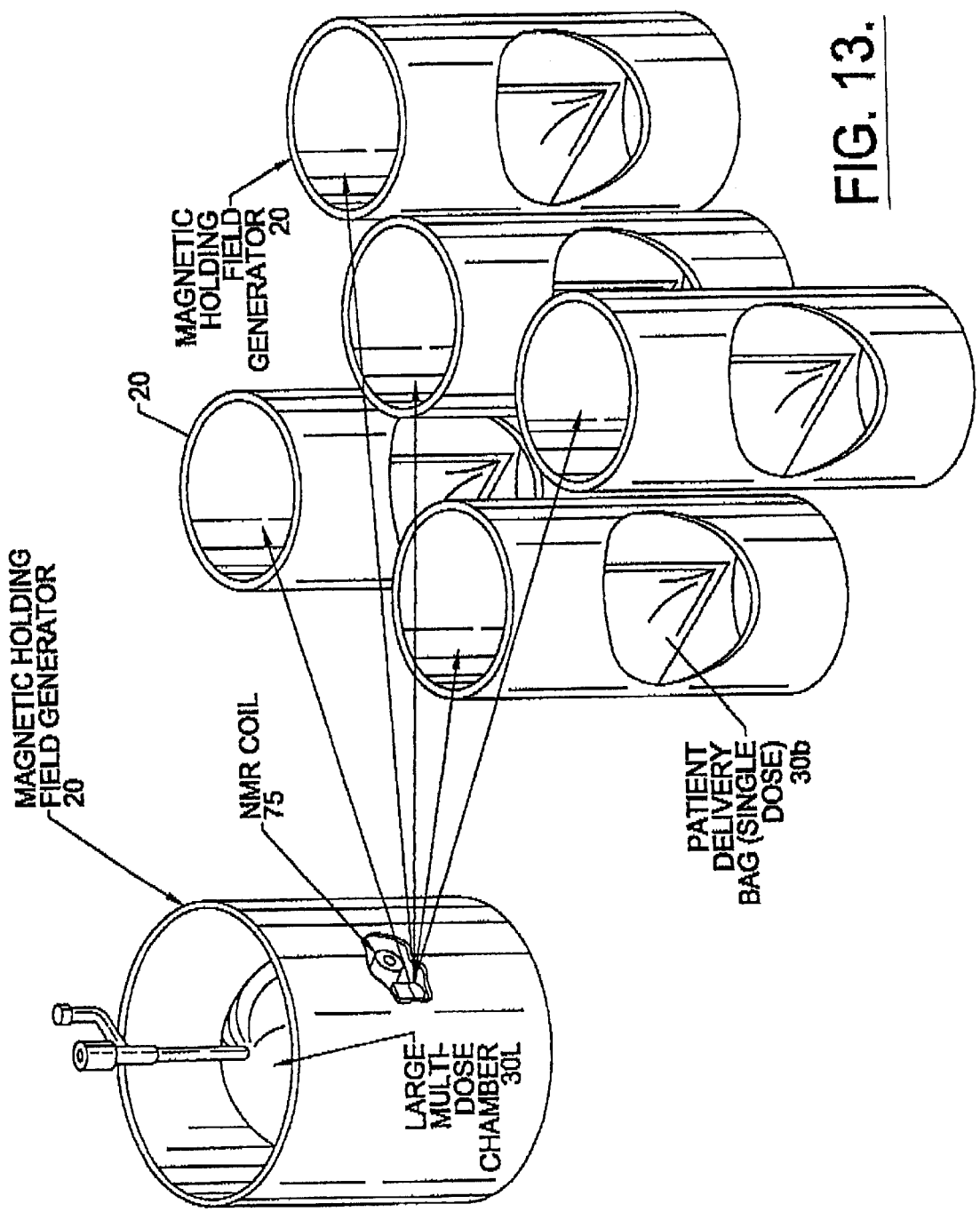
FIG. 13 is a perspective partial cutaway view of a distribution system which employs a plurality of magnetic holding field generators in the second transport unit.

Preferably, the gas chamber 30 is configured to provide a quantity of hyperpolarized gas which can be conveniently delivered to an end point in a user-friendly single dose volume (but of course can also be configured to provide multiple or partial dose quantities) of hyperpolarized gas. In a preferred embodiment, the gas chamber 30 is a 100–200 cm$^3$ gas spherical chamber. For $^3$He, it is preferred that the gas chamber 30 is pressurized to about 4–12 atmospheres of total pressure, and more preferably it is pressurized to about 5–11 atmospheres of total pressure. Pressuring an appropriately sized gas chamber can allow the hyperpolarized gas to be released through the exit as the pressure acts to equalize with ambient conditions. Thus, by merely opening the valve 32, the hyperpolarized gas can be directed to a patient or a patient delivery system with minimal handling (and thus minimal potentially depolarizing interaction). Alternatively, as shown in FIGS. 12A, 12B, and 13 the hyperpolarized gas can be divided and diluted or appropriately sized either at a polarization site or at a second site remote from the polarization site into several patient delivery sized bags with expandable chambers for (further) transport and delivery. The walls of the expandable chamber bags can be depressed to expel the gas mixture held therein with a minimum of extraction equipment required.

It should be noted that for hyperpolarized $^3$He, at about 10 atm of pressure, the theoretical $T_1$ due to interactions with other hyperpolarized nuclei is about 75 hours. Substantially higher pressures allow more gas product to be shipped in the container and reduces the sensitivity of the hyperpolarized gas to gradient relaxation, but the gas-gas collision relaxation can become more prevalent. In contrast, for $^{129}$Xe, it is preferred that the gas pressure be about 10 atm or less, because higher pressures can dramatically reduce the expected relaxation time of the hyperpolarized $^{129}$Xe (i.e., at 10 atm, the $T_1$ is 5.6 hours).

In a preferred embodiment of the instant invention, as shown in FIG. 4, the gas chamber 30 includes a capillary stem 35 which is sized and configured to minimize the travel of hyperpolarized gas atoms out of the spherical volume and acts to keep most of the hyperpolarized gas away from the valve 32. More specifically, the capillary is dimensioned such that the ratio of the main body volume to the capillary volume, multiplied by the diffusion time of $^3$He (at fill pressure) to go twice the length of the capillary, is greater than the desired $T_1$. As such, a major portion of the hyperpolarized gas remains in the region of highest homogeneity within the solenoid 20 where it is best protected from depolarizing effects during transport. Preferably, the capillary stem 35 includes about a 1.0 mm inside diameter and has a length, which is sufficient to allow proper positioning of the sphere within the region of homogeneity in the solenoid 20. In the preferred embodiment of the solenoid 20 described above, the capillary stem 35 is approximately 4 inches long. As such, for a gas chamber 30 with a three inch diameter sphere, the capillary stem 35 is preferably longer than the than the sphere holding (body) portion 33 of the gas chamber 30. Also preferably, the inner diameter of the capillary stem 35 is sufficiently small as to slow movement of the hyperpolarized atoms relative to the valve 32, thereby keeping a substantial portion of the hyperpolarized gas in the spherical volume 33 and thus within the high-homogeneous field region.

As also discussed above, even if the transport unit 10 shields or protects the hyperpolarized gas from EMI and static magnetic field gradients, the surface relaxation rate associated with the container, the valve(s), and other hyperpolarized gas contacting components can deleteriously affect the polarization lifetime of the hyperpolarized gas. As such, particularly for hyperpolarized $^3$He, and for multi-dose containers 30L (FIGS. 12A, 13) it is preferred that the gas chamber 30 primarily comprise an aluminosilicate material. Aluminosilicate materials have been shown to have long surface relaxation times. The gas chamber 30 may be manufactured from GE180™, although, of course, other aluminosilicates may be used. Typically a transition glass is used to attach the borosilicate (Pyrex®) valve 32 of the aluminosilicate gas chamber 30. Suitable valves 32 for use in the gas chambers 30 is part number 826460-0004 which is available from Kimble Kontes, located in Vineland, N.J. The valves 32 can be further modified to coat or replace any paramagnetic or ferromagnetic impurities, or may be treated or conditioned to remove or minimize the amount of impure or depolarizing materials that are positioned proximate to the hyperpolarized gas. Suitable transition glass includes uranium glass.

Alternatively, other polarization-friendly materials can be used, such as high purity metals or polymers with metallized surfaces, polymers and the like. "High purity" as used herein means materials that are substantially free of paramagnetic or ferrous materials. Preferably, the metallic materials include less than 1 part per million paramagnetic or ferrous impurities (such as iron, nickel, chromium, cobalt and the like). In an alternate preferred embodiment, as shown in FIGS. 12A and 13, the gas chamber can be a resilient bag 30b such as a single or multiple polymer layer bag having a metallic film layer or inner surface or surface layer which is formed from one or a combination of a high purity metal such as gold, aluminum, indium, zinc, tin, copper, bismuth, silver, niobium, and oxides thereof. Additional descriptions of preferred hyperpolarization materials and containers, O-rings and the like are included in co-pending U.S. patent application Ser. No. 09/126,448 entitled "Containers for Hyperpolarized Gases and Associated Methods" (and its related application) as discussed under the Surface-induced Relaxation section hereinabove. The resilient bag 30b may include a capillary stem (not shown) and/or a fluid port isolation means to inhibit the hyperpolarized gas from contacting potentially depolarizing valves and fittings during transport or storage.

It is also preferred that the gas chamber 30 be configured as a sphere because it has a geometry that minimizes the surface area/volume ratio and thus the surface-induced contact relaxation. Further, since the solenoid 20 described above generates a region of high homogeneity that is typically generally spherical in shape, making the gas chamber spherical in shape maximizes the volume of the gas chamber that fits the homogeneous region.

In another preferred embodiment, the transport unit 10 is configured in at least two different sizes, a first size for transporting large quantities of gas in a single container, and a second size for transporting one or more (preferably a plurality of single-sized dosages) for facilitating distribution of single-use doses of hyperpolarized substances or formulations at remote sites to retain sufficient polarization to allow clinical useful images over longer transport distances and elapsed times from original the original point of polarization. FIGS. 12A, and 13 illustrate a multi-bolus or dose container 30L (i.e., a relatively large capacity container) and a plurality of smaller resilient bag 30b containers (i.e., bags with expandable chambers). The bag container 30b may include a capillary stem similar to that used for the rigid container 30 discussed above (not shown). Similar, to the gas chamber 30, the NMR coil 75 can be positioned on an outer surface thereof to monitor polarization during transport. Further details regarding preferred bag materials and configurations are discussed in do-pending and co-assigned U.S. Patent Application entitled, "Resilient Containers for Hyperpolarized Gases and Associated Methods," identified by Attorney Docket No. 5770-12IP and related U.S. patent application Ser. No. 09/126,448, incorporated by reference herein.

The multi-bolus container 30L is used to dispense desired formulations, concentrations, and/or mixtures of the hyperpolarized gas (with or without other substances, liquids, gases (such as nitrogen), or solids) at a remote site. The multi-dose container 30L may be the polarization chamber or optical cell itself. The magnetic field generator is preferably a correspondingly sized solenoid 20, but can also be provided by permanent field magnets (not shown). Of course, a single sized transport unit (or even the same transport unit) can be used to transport the hyperpolarized gas to the second and third sites, i.e., the second transport unit 10s may be sized and configured the same as the first transport unit 10f as needed. Alternatively, the first transport unit may be larger than the second or the second may be larger than the first depending on how the hyperpolarized gas is distributed and the shape and size and number of the second containers positioned for transport from the second site.

FIG. 13 illustrates that the resilient bags 30b can each have an individual magnetic field generator shown as a solenoid 20 operatively associated therewith. FIG. 12A illustrates one alternate configuration with a single magnetic field generator (also shown as a solenoid 20) sized and configured to hold a plurality of bags 30b therein. As shown in FIG. 12B, a tray 630 can be used to hold a plurality of hyperpolarized substance filled bags and translated into the solenoid 20' to position them in the desired region within the solenoid for effective shielding as discussed above. The tray 630 can also facilitate removal at a delivery site. Preferably, the tray is formed of non-conductive polarization friendly materials. Of course, the tray 630 can be alternatively configured such as with compartments and sliding and locking means which ratchet or lock for positionally affirmatively locating the bags, as well as a handle or extension means to allow central or recessed positioning of the tray and bags within the desired region of homogeneity.

Operating Circuitry

Figure 7:
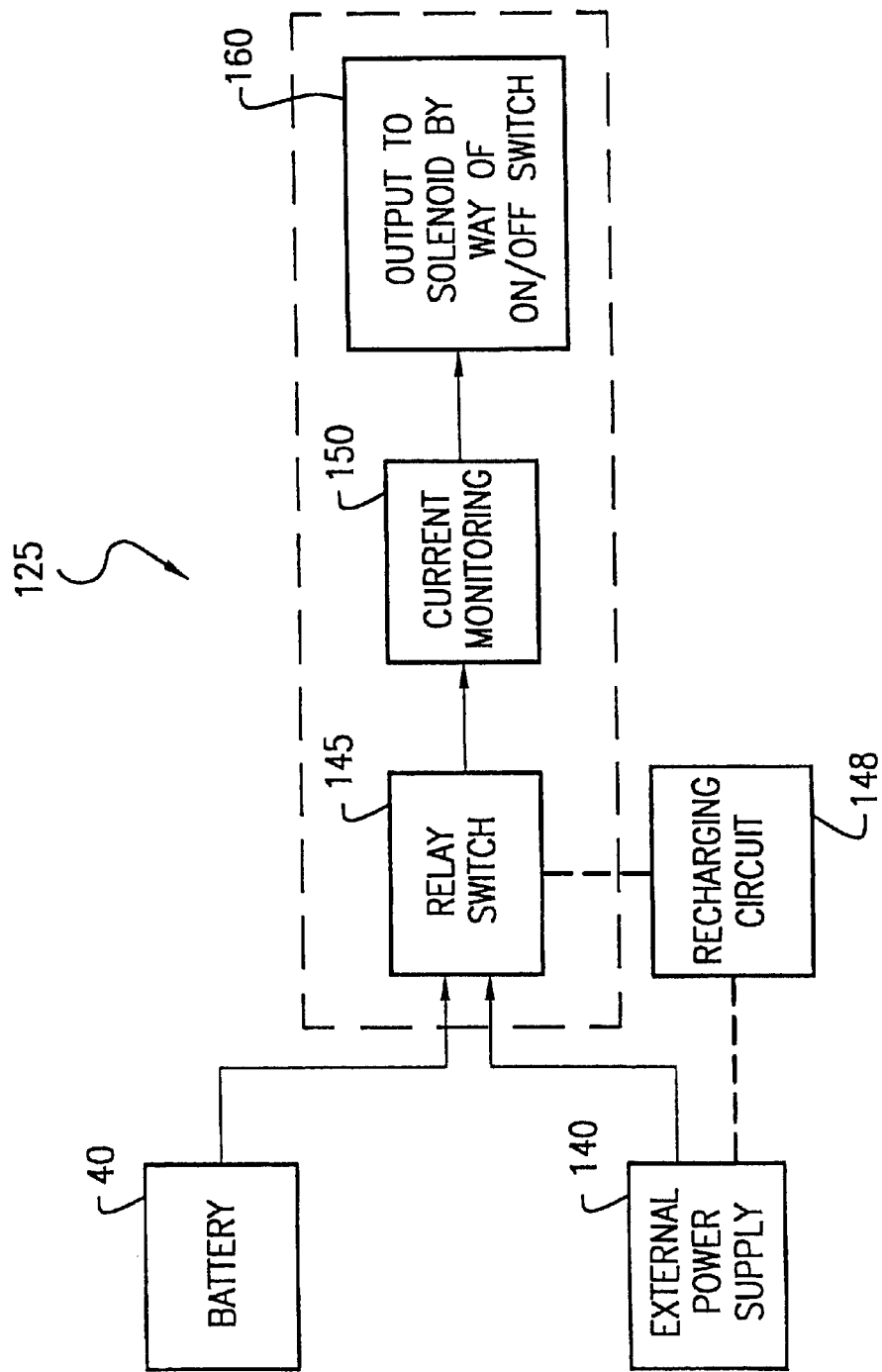
FIG. 7 is a schematic illustration of a power monitoring and switching circuit for use with a portable transport unit according to the present invention.

Preferably, the transport unit 10 includes operating circuitry 50 that is operably associated with the solenoid 20 and the power source 40. Preferably, the internal power source 40 is a battery as described above, but can also be operably associated with an external power source via an external power connection 141 (FIG. 5). As shown schematically in FIG. 8, the operating circuitry 50 preferably includes a power monitoring switching circuit 125. As shown in FIG. 7, the power monitoring and switching circuit 125 includes a relay switch 145, a current monitor 150 and an on/off switch output 160 which is connected to the input of the current load into the solenoid 20. Advantageously, the power monitoring circuitry 125 is preferably configured to automatically switch between the different power sources (40, 140) without interruption of the current to either the operating circuitry 50 or the solenoid 20. Preferably, the power monitoring switching circuit 125 manages the power supply such that the transport unit 10 is powered from the internal power source 40 (battery) only when needed. For example, when the transport unit 10 is not easily connected to an external power source 140, the power monitoring circuit 125 engages the battery 40 to supply the power to the transport unit 10. Preferably, the power monitoring circuit 125 then disengages the battery 40 when the transport unit 10 is connected to a viable external power source 140 (such as a wall or vehicle power outlet) when the external connector port 141 is connected to the external source 140. In a preferred embodiment, as shown in FIG. 7, the power monitoring circuit 125 is operably associated with recharging circuit 148 which allows the internal battery 40 to be recharged when the transporter is powered from an external supply 140.

Figure 8:
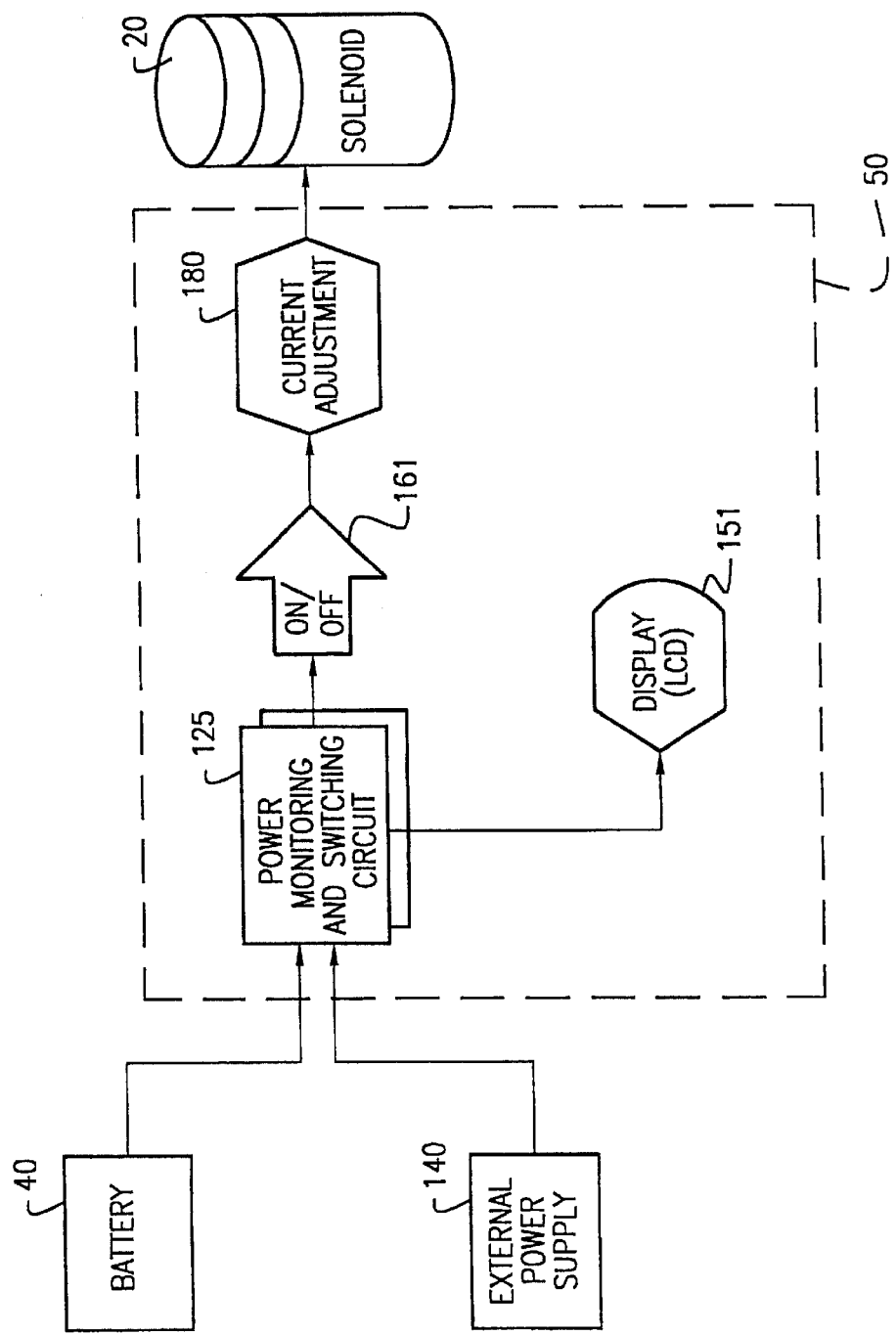
FIG. 8 is a schematic illustration of an operating circuit for use with a portable transport unit associated with a preferred embodiment of the present invention.

Of course, the operating circuit 50 can also include other components and circuits such as a battery monitor 171 (FIG. 5) and an audible and or visual alarm (not shown) to indicate when the battery 40 is low. Preferably, as also shown in FIGS. 5 and 8, the transport unit 10 includes a current readout 151 associated with the power monitoring circuit 125. As shown, the current readout is a LCD display 151, which will allow a custodian to visually affirm that the transport unit is functioning properly and enable him to monitor the current running through the solenoid. Also as shown in FIG. 8, the operating circuitry 50 preferably includes a current adjustment means 180 for increasing or decreasing the current delivered to the solenoid 20. In a preferred embodiment, the current adjustment means 180 is a rheostat operated by the current control knob 180 (FIG. 5). As discussed above, the adjustable current means preferably is adjustable to supply between about 100 mA to about 2.0A.

The current adjustment allows the operating circuitry 50 to adjust the current in response to the needs of the transport unit 10. For example, the current can be adjusted to provide a custom holding field corresponding to the type of hyperpolarized gas being transported. Additionally, the current to the solenoid 20 can be adjusted to compensate for electronic or mechanical system variation (i.e., battery drainage, electronic drift, coil resistance variability due to temperature), thereby maintaining the desired holding field strength. The operating circuit preferably includes a means for adjusting the magnetic field strength of the magnetic holding field, which preferably operates to shift the Larmor frequency of the spins associated with the hyperpolarized gas. Such magnetic field adjustability is useful for performing of NMR measurements, or to avoid electromagnetic interference at a particular frequency or frequency range. The NMR measurement system will be discussed further below.

As with all materials that contact, or are positioned near or proximate to the hyperpolarized gas, it is preferred that the operating circuitry 50 contain minimal magnetically active materials and components such as iron transformers. However, if such materials or components are used, then it is preferred that they be positioned a sufficient distance from the gas chamber 30 and the solenoid 20 so that they do not cause undue gradient relaxation. Further, it is preferred that temperature sensitive components be removed from the operating circuit 50 in order to provide a reliable, consistent circuit which can tolerate broad temperature ranges (inside and outside). Of course the operating circuitry 50 may be present in hardware, software, or a combination of software and hardware.

Portable Monitoring (NMR Coil/Polarimetry)

Preferably, the transport unit 10 is operably associated with a polarization monitoring system that is configured to monitor the polarization level of the hyperpolarized gas in the gas chamber 30. Advantageously, such system can be used in transit or at a desired evaluation site. For example, prior to release of the gas from the transport unit 10, the monitoring system can acquire a signal corresponding to the polarization level of the hyperpolarized gas in the transport unit 10 and thus indicate the viability of the gas prior to delivery or at a receiving station at the point of use. This can confirm (reliably "inspect") the product and assure that the product meets purchase specification prior to acceptance at the use site.

The polarization monitoring system can also be used with the transport unit 10 to evaluate magnetic holding field fluctuations during transport. Further, the monitoring system can automatically adjust the current to compensate for detected fluctuations. Additional details of a suitable monitoring systems and methods for implementing same are discussed in co-pending and co-assigned U.S. Patent Application, entitled "Portable Hyperpolarized Gas Monitoring System, Computer Program Products, and Related Methods," identified by Attorney Docket No. 5770-17. The contents of this application are hereby incorporated by reference as if recited in fill herein.

As shown in FIG. 1, the transport unit 10 preferably includes a NMR transmit/receive coil 75, which is positioned such that it (securely or firmly) contacts the external wall of the storage chamber 30. The NMR coil 75 includes an input/output line 375 that is operably associated with a NMR polarimetry circuit and a computer (typically an external portable computer device 500, as shown in FIG. 5). Preferably, the transport unit 10 includes a computer access port 300 which is operably associated with the operating circuitry 50 and the NMR coil 75 via the coaxial BNC bulkhead 275. The NMR coil 75 can be used with the monitoring system to evaluate the polarization level of the hyperpolarized gas in a substantially nondestructive evaluation technique.

Figure 9:
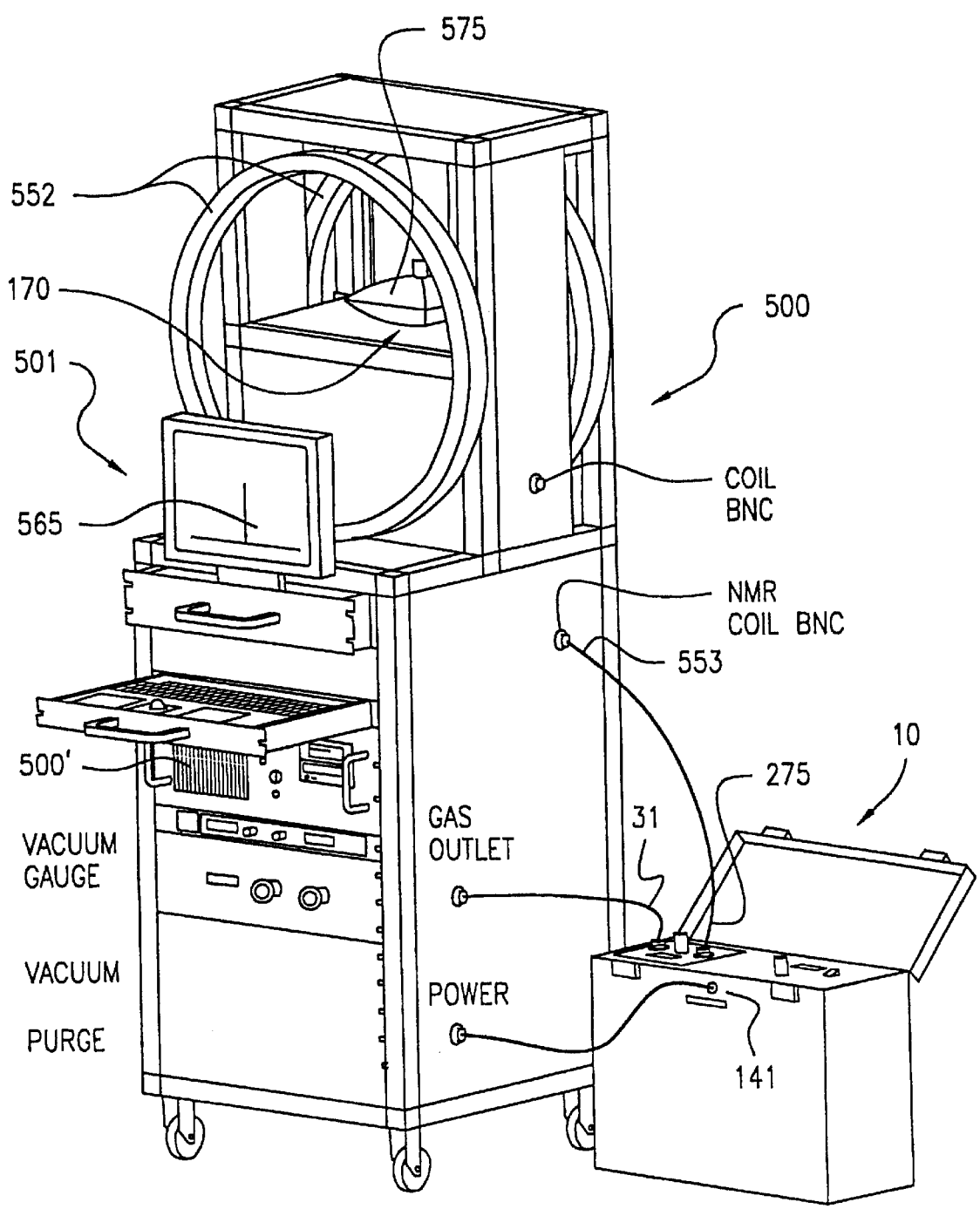
FIG. 9 is a front perspective view of a calibration/docking station according to the present invention.

Alternatively, or in addition to the (portable) monitoring system, the transport unit 10 is preferably configured to conveniently dock into a (remote) site calibration station 500, as shown in FIG. 9. Generally described, as shown in FIG. 9, the polarization detection can be carried out at a calibration station 500 which preferably uses a low-field NMR spectrometer to transmit RF pulses to surface coils 75 positioned proximate to the hyperpolarized gas sample. The spectrometer then receives at least one signal back from the NMR coil 75 corresponding to the hyperpolarized gas. The signal is processed and displayed 565 to determine the polarization level of the hyperpolarized gas (preferably this reading is taken while the gas is contained in the gas chamber 30 within the transport unit 10).

As shown, the calibration station 500 preferably includes a set of Helmholtz coils 552 (preferably of about 24 inches in diameter) to provide the low magnetic field and another external NMR surface coil (not shown). The additional NMR surface coil is preferably sized and configured at about 1 inch in diameter and with about 350 turns. The NMR surface coil is configured to be received into a non-metallic platform 170 and is arranged to be substantially flush with the upper surface of the platform to be able to contact the patient delivery vessel 575. Also, the NMR coil is preferably positioned in the center of the Helmholtz coils 552. The term "low field" as used herein includes a magnetic field under about 100 Gauss. Preferably, the calibration station 500 is configured with a field strength of about 5–40 Gauss, and more preferably a field strength of about 20 Gauss. Accordingly, the corresponding $^3$He signal frequency range is about 16 kHz–128 kHz, with a preferred frequency of about 64 kHz. Similarly, the $^{129}$Xe signal frequency range is about 5.9 kHz–47 kHz, with a preferred signal frequency of about 24 kHz.

Preferably, the hyperpolarized gas is contained in a patient delivery bag container 30b which is positioned on the top surface of the surface coil (not shown) and substantially in the center of the Helmholtz coils 552. Generally described, in operation, a selected RF pulse (of predetermined frequency, amplitude, and duration) is transmitted from the NMR device 501 to the surface coil (not shown). Alternatively, the calibration station 500 can be used to transmit the selected RF pulse inside the transport unit 10 via connection 553. In any event, the RF pulse frequency corresponds to the field strength of the magnetic field and the particular gas, examples of which are noted above. This RF pulse generates an oscillating magnetic field which misaligns a small fraction of the hyperpolarized $^3$He or $^{129}$Xe nuclei from their static magnetic field alignment. The misaligned nuclei start precessing at their associated Larmour frequency (corresponding to pulse frequency). The precessing spins induce a voltage in the surface coil that can be processed to represent a signal 565. The voltage is received back (typically amplified) at the computer and the signal fits an exponentially decaying sinusoid pattern. (As shown, the displayed signal 565 is the Fourier transform of the received signal). The initial peak-to-peak voltage of this signal is directly proportional to polarization (using a known calibration constant). The computer 500' can then calculate the polarization level and generate calculated preferred use dates and times associated with desired polarization levels. As will be recognized by those of skill in the art, other calibration or hyperpolarization level determination methods can also be employed and still be within the product identification and calibration or product-use or expiration determination methods contemplated by the present invention. For example, by detecting the minute magnetic field generated by the polarized $^3$He spins, one can determine a polarization level associated therewith.

Figure 6:
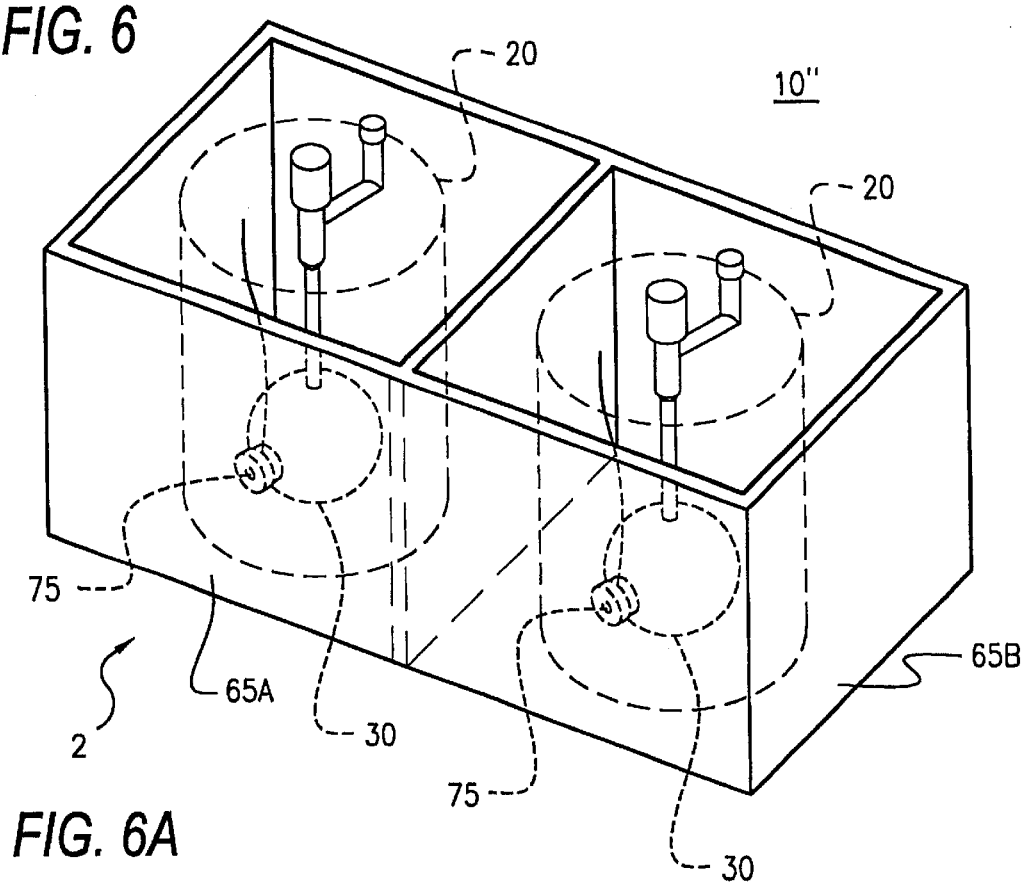
FIGS. 6, 6A, and 6B are perspective views of transport units configured to transport multiple containers of hyperpolarized gas products according to alternate embodiments of the present invention.
Figure 6A:
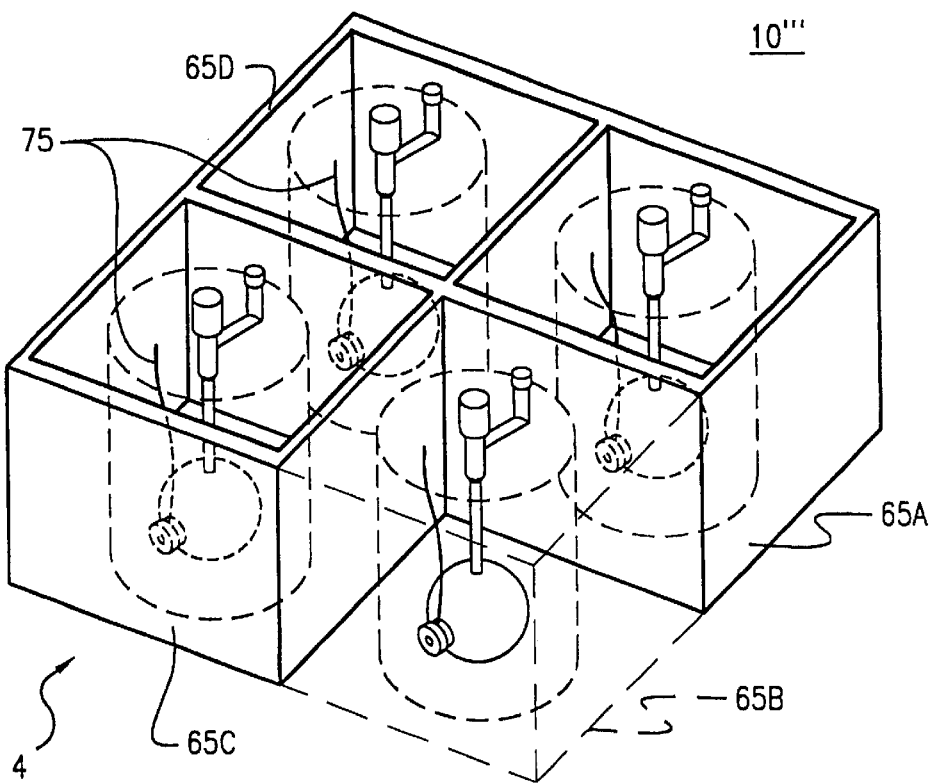
Figure 6B:
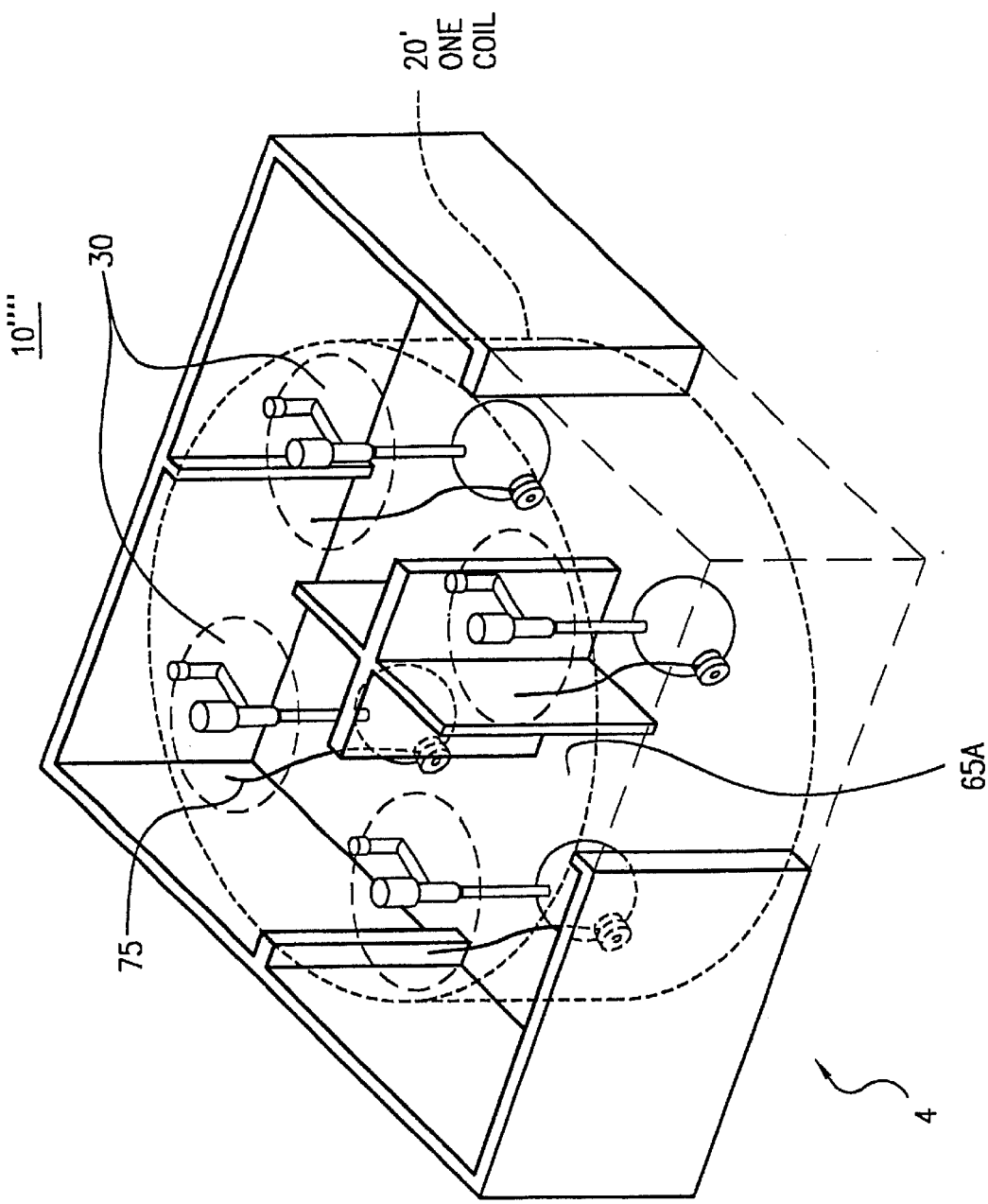

In an alternate embodiment, the transport units 10", 10''' comprise a plurality of gas chambers 30 (FIGS. 6, 6A) or 30b (FIG. 12A and 13) and each gas chamber 30 preferably includes an individual NMR coil 75 which is positioned adjacent each gas chamber within the solenoids of the transport unit 10", 10'''. It is further preferred that each gas chamber 30 be substantially electrically isolated from the other gas chambers 30 such that each gas chamber 30 is individually monitorable (individually excitable) for hyperpolarization level and each is individually tunable (adjustable field strength and coil current). In another alternate embodiment, as shown in FIG. 6B, the transport unit 10" can be configured with a single coil 20' which is sized and configured to surround a plurality of gas chambers 30 therein (see also FIG. 12A). When positioning the containers 30 within the transport units (if the containers have necks or capillary stems, whether for single or multiple gas container units), neck or stem orientation can be oriented in different directions. Further, although the transport units shown in FIGS. 6, 6A, and 6B illustrate side by side gas containers, the present invention is not limited thereto. For example, the transport unit can be configured to comprise a plurality of units that are stacked longitudinally with capillary stems extending in the same or opposing directions. FIG. 12A illustrates one example, a plurality of bags 30b positioned in substantial linear alignment (whether longitudinal or lateral). An NMR coil 75 can also be attached to each bag 30b held for transport or storage (not shown).

Advantageously, a transport unit comprising a solenoid 20 has successfully supported a $T_1$ of $^3$He of 45 hours (valved gas chamber) while an unvalued model (sealed) gas chamber (pressurized to about 2.2 atm, not shown) has supported a $T_1$ of 120 hours. These exemplary $T_1$'s were for $^3$He polarized at a production site and transported in the transport unit 10 for a travel time of about 30 hours (approximately 28 hours where the unit was physically removed from its "home-base" or polarizer) and where the unit was actually in transit for approximately 10 hours. The gas chambers 30 in the transport unit 10 were exposed to environmental conditions while traveling to a use site in a vehicle.

Central Production Site Remote Use Site

Use of a remote polarization production site typically requires longer $T_1$'s relative to an on-site polarization apparatus to allow adequate shipping and transport times. However, a centrally stationed polarizer can reduce equipment and maintenance costs associated with a plurality of on-site units positioned at each imaging site and the transport units of the instant invention can allow increased transport times with longer $T_1$ times over those conventionally achieved. In a preferred embodiment, a production polarizer unit (not shown) generates the polarized gas a production site. The gas chamber 30 (or 30b) is in fluid communication with the polarizer unit such that the polarizer unit produces and directs the polarized gas to the gas chamber 30. Preferably, the gas chamber 30 is held in the transport unit enclosure 65 (FIG. 1) (or individual enclosure 65A–D, FIGS. 6, 6A, and 6B) during the filling step. More preferably, the container is positioned in the transport unit within the homogeneous holding field therein prior to the filling step. After a sufficient quantity of hyperpolarized gas is captured in the gas chamber 30, the valve 32 is then closed (the gas chamber is sealed). Thus, the solenoid 20 in the transport unit 10 is activated (preferably prior to the filling step, but can also be activated after the container is sealed, if the container is otherwise protected such as on-board the polarizer unit during fill. In operation, the power switch 161 (FIG. 5) on the transport unit 10 is turned to the "on" position and electrical current is supplied to the solenoid 20 such that about a 7 Gauss magnetic holding field is generated as discussed above. The hyperpolarized gas is shielded from stray magnetic gradients within the transport unit 10 until and after delivery to a remotely located site. When desired, the hyperpolarized gas can be directed or released from the gas chamber 30 and dispensed to a patient via some patient delivery system (temporally limited to its end use time) such that the hyperpolarized state of the gas at delivery is sufficient to produce useful clinical images.

Another aspect of the present invention is a system for distributing hyperpolarized gas products such that single use or patient sized doses of hyperpolarized gases have increased shelf life or useful polarization life. The system includes a first transport unit 10f (schematically shown by dotted line box in FIG. 12A) which is sized and configured to hold at least one multi-dose container 30L therein. The system also includes at least one second transport unit 10s (schematically shown in FIG. 12A)sized and configured to carry a plurality of single dose containers (such as for example shown by 30 or 30b in FIGS. 6A, 6B, and 12A, 13, respectively) therein. Preferably, the multi-dose container is a rigid body container 30L and the single dose containers are resilient containers 30b having expandable chambers to allow easy delivery or administration at a use site as described above. In a preferred distribution system, the hyperpolarized gas is collected in a multi-bolus container (such as that shown as container 30L in FIGS. 12A, 12B, and 13) at the polarization site and transported in a suitably sized transport unit 10f to a second site remote from the first site. This multi-bolus container 30L can be the optical cell itself, or other suitable container configuration such as those discussed above.

In one embodiment, as shown in FIG. 12A, the multi-dose container 30L is transported to a pharmaceutical distribution point where the hyperpolarized gas in the multi-dose container 30L can be dispensed or formulated into the proper dosage or mixture according to standard pharmacy or drug manufacturer operation. For example, but not limited to, this dispensing or formulation activity may include solubilizing the gas in a carrier liquid, adjusting the concentration, preparing the mixture for injection or inhalation or other administration as specified by a regulatory agency directive or physician, or combining one or more different gases or liquids or other substances with the transported hyperpolarized gas. Preferably, the materials used to form the product are suitable for administration to an in vivo subject (pharmaceutical grade substance). In any event, at the second site, the hyperpolarized gas held in the multi-bolus container 30L is preferably dispensed into single use, application-sized, or prescripted amounts or doses of hyperpolarized product into proportionately sized resilient containers 30b. Proper conditioning of the bag containers 30b is preferably observed as will be discussed further below.

Subsequent to the dispensing step, the second or subsequent (preferably) single-use sized container can be delivered to a proximately located use site (if the second site is proximate or part of a clinical use site such as a hospital). Alternatively, at the second site, at least one bag 30b is positioned in a second transport unit 10 which is suitably sized and configured to hold the bag therein. Preferably, the transport unit 10s is configured to hold a plurality of bags as shown in FIGS. 12A, 12B. In any event, one or more bags are positioned in a second transporting unit 10s and delivered or transported to a third or tertiary site, preferably the clinical use site. Preferably, for bag containers, the transport unit 10s includes a magnetic field generator with a region of high homogeneity. Preferably, the high homogeneity is such that the gradients are less than about $10^{-3}$ cm$^{-1}$ over the volume occupied by the bags 30b.

In a preferred embodiment, the first transport distance is such that the hyperpolarized gas is moved at increased times or distances over conventional uses. Preferably, the transport units and associated container of the present invention are configured such that during transport and/or storage, the hyperpolarized gas (particularly $^3$He) retains sufficient polarization after about at least 10 hours from polarization, and more preferably after about at least 14 hours, and even more preferably greater than about 30 hours after polarization and when transported to a second site (and even then a third or tertiary site). Further, the transport unit and associated containers are preferably configured to allow greater transit distances or times from the original polarization point in a manner in which the hyperpolarized product retains sufficient polarization to provide clinically useful images. This distribution system is in contrast to the conventional procedure, whereby the hyperpolarized gas is produced at a polarization site and rushed to a use site (which is typically relatively close to the polarization site).

Preconditioning the Container

Preferably, due to susceptibility of the hyperpolarized gas to paramagnetic oxygen as noted above, the gas chamber 30 is preconditioned to remove contaminants. That is, it is processed to reduce or remove the paramagnetic gases such as oxygen from within the chamber and container walls. For containers made with rigid substrates, such as Pyrex™, UHV vacuum pumps can be connected to the container to extract the oxygen. Alternatively, for rigid and/or resilient containers (such as polymer bag containers), a roughing pump can be used which is typically cheaper and easier than the UHV vacuum pump based process. Preferably, for resilient bag containers, the bag is processed with several purge/pump cycles. Preferably this is accomplished by pumping at or below 40 mtorr for one minute, and then directing clean (UHP) buffer gas (such as nitrogen) into the container at a pressure of about one atmosphere or until the bag is substantially inflated. The oxygen partial pressure is then reduced in the container. This can be done with a vacuum but it is preferred that it be done with nitrogen. Once the oxygen realizes the partial pressure imbalance across the container walls, it will outgas to re-establish equilibrium. Typical oxygen solubilities are on the order of 0.01–0.05; thus, 95–99% of the oxygen trapped in the walls will transition to a gas phase. Prior to use, the container is evacuated, thus harmlessly removing the gaseous oxygen. Unlike conventional rigid containers, polymer bag containers can continue to outgas (trapped gases can migrate therein because of pressure differentials between the outer surface and the inner surface) even after the initial purge/pump cycles. Thus, care should be taken to minimize this behavior, especially when the final filling is not temporally performed with the preconditioning of the container. Preferably, a quantity of clean (UHP or Grade 5 nitrogen) filler gas is directed into the bag (to substantially equalize the pressure between the chamber and ambient conditions) and sealed for storage in order to minimize the amount of further outgassing that may occur when the bag is stored and exposed to ambient conditions. This should substantially stabilize or minimize any further outgassing of the polymer or container wall materials. In any event, the filler gas is preferably removed (evacuated) prior to final filling with the hyperpolarized gas. Advantageously, the container of the instant invention can be economically reprocessed (purged, cleaned, etc.) and reused to ship additional quantities of hyperpolarized gases.

It is also preferred that the container or bag be sterilized prior to introducing the hyperpolarized product therein. As used herein, the term "sterilized" includes cleaning containers and contact surfaces such that the container is sufficiently clean to inhibit contamination of the product so that it is suitable for medical and medicinal purposes. In this way, the sterilized container allows for a substantially sterile and non-toxic hyperpolarized product to be delivered for in vivo introduction into the patient. Suitable sterilization and cleaning methods are well known to those of skill in the art.

Hyperpolarized Gas Transport Protection System Examples

Figure 11:
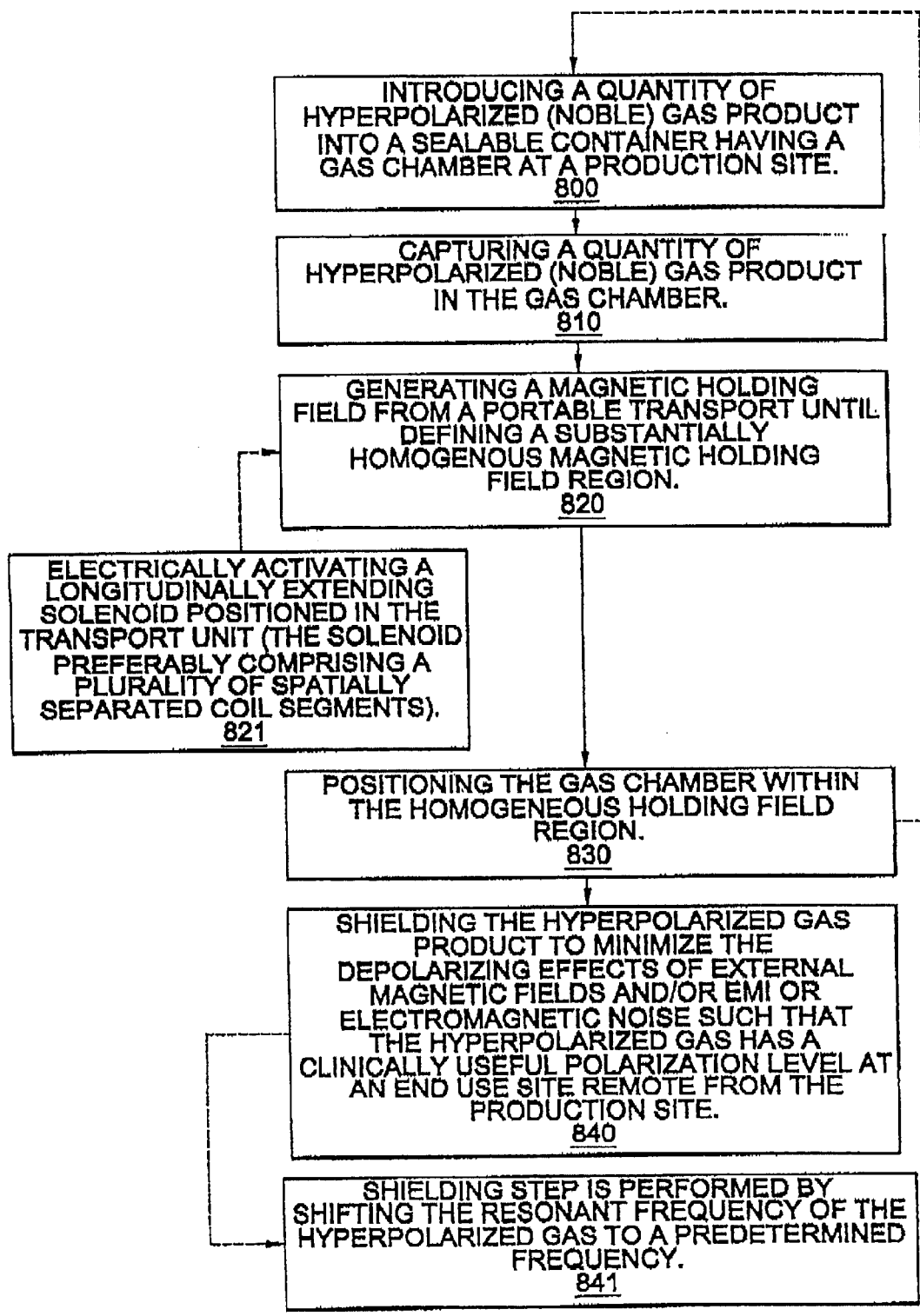
FIG. 11 is a flow chart of a system for shielding hyperpolarized gas from the depolarizing effects attributed to external magnetic fields during transport, thereby preserving the polarized life of the gas.

FIG. 11 illustrates a preferred system for protecting hyperpolarized (noble) gases (and hyperpolarized gas products in whatever form such as fluids, liquids, solids, and the like including other gas or liquid components in whatever form as noted earlier). A quantity of hyperpolarized gas product is introduced into a sealable container comprising a gas chamber (and preferably a capillary stem) at a production site (Block 800). A quantity of a hyperpolarized gas is captured in the gas chamber (Block 810). A magnetic holding field is generated from a portable transport unit thereby defining a substantially homogeneous magnetic holding field region (Block 820). The gas chamber is positioned within the homogeneous holding region (Block 830). Preferably, (as indicated by dotted line) the gas chamber is positioned in the magnetic field holding region prior to filling. The hyperpolarized gas product is shielded from stray magnetic fields to minimize the depolarizing effects attributed thereto such that the hyperpolarized gas retains a clinically useful polarization level at an end use site remote from the production site (Block 840). Preferably, the magnetic holding field step is provided by electrically activating a longitudinally extending solenoid positioned in the transport unit. The solenoid comprises a plurality of spatially separated coil segments (Block 821). It is also preferred that the shielding step be performed by shifting the resonance frequency of the hyperpolarized gas in the container to a predetermined frequency as discussed above (Block 841).

Figure 14:
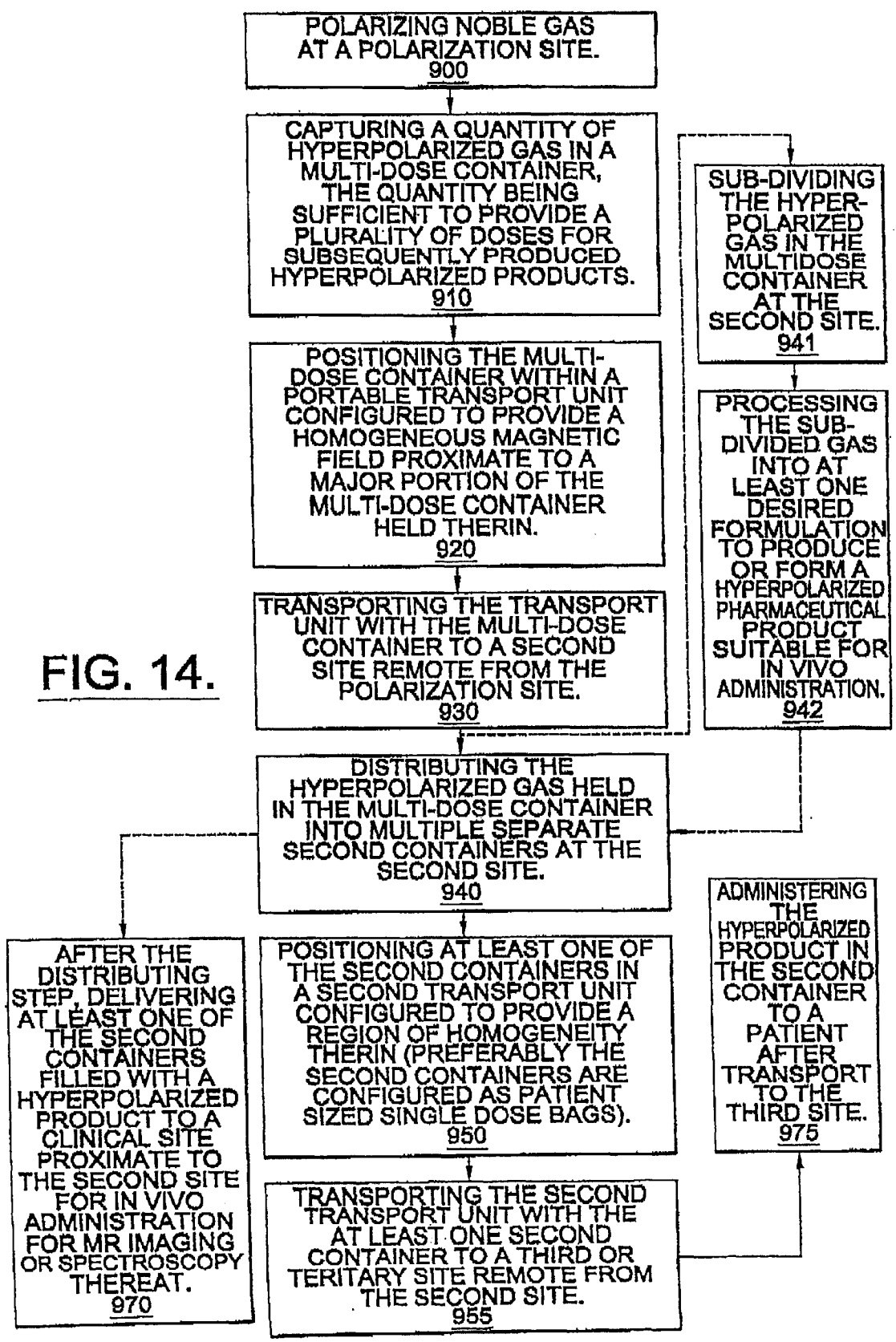
FIG. 14 is a flow chart of a distribution system according to the present invention.

FIG. 14 illustrates a method and/or system for distributing hyperpolarized gas products. Noble gas is polarized at a polarization site (Block 900). A quantity of hyperpolarized gas sufficient to provide multiple doses of hyperpolarized noble gas products are captured in a multi-dose container (Block 910). The multi-dose container is positioned in a portable transport unit which is configured to provide a homogeneous magnetic field for holding a major portion of the multi-dose container therein (Block 920). The multi-dose container in the transport unit is transported to a second site remote from the first or polarization site (Block 930). At the second site, the hyperpolarized gas in the multi-dose container is distributed into multiple separate second containers (preferably reduced or patient sized dose containers), and more preferably single dose bags (Block 940).

Preferably, at the second site, and also preferably prior to the distribution step (Block 940), the multi-doses of gas are subdivided (Block 941) and processed into at least one desired formulation to form a hyperpolarized pharmaceutical grade product suitable for in vivo administration (Block 942). Preferably, the processing and subdividing steps are performed prior to the distribution of the gas into the secondary containers for transport. Thus, the processing and/or distribution step at the second site can include the steps of formulating or otherwise processing the hyperpolarized gas into a sterile or non-toxic product such that it is suitable for in vivo human administration. The processing can include diluting concentration such as by adding other inert gases (such as substantially pure, at least grade 5, nitrogen), or carrier or other liquids or substances. The processing can include manipulating the hyperpolarized gas from the multi-dose container such that it is formulated into the proper dosage or mixture according to standard pharmaceutical industry operation. This may include solubilizing the gas, adjusting the concentration, preparing the mixture for injection or inhalation or other administration as specified by a physician, or combining one or more different gases or liquids or other substances with the transported hyperpolarized gas. Then, the formulated hyperpolarized product, substance, or mixture is preferably dispensed into at least one second container, and preferably into a plurality of preferably single use size resilient containers which can be transported to a third or tertiary site.

From the second site, at least one of the second containers (preferably a single dose bag container) can be used to deliver a hyperpolarized product to a user proximate to the second site (Block 970) or positioned within a second transport unit with a region of homogeneity (Block 950) and transported to a third site (preferably an imaging site) remote from the second site (Block 955). The delivery of the product at a site proximate to the second site is especially applicable for distribution-oriented second sites which are clinics (such as a wing of the hospital) The hyperpolarized product can then be administered to a patient at the imaging site or stored for futures use (Block 975). The administered hyperpolarized product is useful for obtaining clinical data associated with Magnetic Resonance Imaging and Spectroscopy procedures. The transport units according to the present invention are configured such that during transport and/or storage the gas has proper shielding as described herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention, Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A solenoid for providing a magnetic field to shield hyperpolarized gases and to reduce the depolarization effects on such gases associated with exposure to stray magnetic field gradients or time dependent electromagnetic fields (EMI), comprising:

a cylindrical body having at least one coil segment thereon, said cylindrical body sized and configured to receive a container holding a quantity of hyperpolarized gas therein; and a power source operably associated with said at least one coil segment, wherein, in operation, current from said power source is directed into said solenoid at said at least one coil segment to generate a magnetic holding field having a low field strength and sufficient homogeneity to shield a quantity of hyperpolarized gas from stray magnetic field gradients or EMI to thereby reduce the depolarization affects associated therewith.

2. A solenoid according to claim 1, wherein said at least one coil segment comprises:

a first coil segment having a first coil length and a first number of windings disposed on said cylindrical body;

a second coil segment having a second coil length and a second number of windings disposed on said cylindrical body adjacent said first coil segment; and a third coil segment having a third coil length and a third number of windings disposed on said cylindrical body adjacent said second coil segment opposing said first coil segment.

3. A solenoid according to claim 2, wherein said first, second, and third coil segments are arranged on said cylindrical body such that each is spatially separate from the other.

4. A solenoid according to claim 3, wherein said second coil length is greater than said first and third coil lengths.

5. A solenoid according to claim 2, wherein said first and third number of windings per unit length are greater than said second number of windings.

6. A solenoid according to claim 2, wherein said second coil segment has about 1.5 times the number of windings of either of the first and third segments.

7. A solenoid according to claim 2, wherein in operation said solenoid defines a magnetic holding field having a magnetic field strength of between about 2–40 Gauss.

8. A solenoid according to claim 7, wherein said power source comprises a battery for portable operation.

9. A solenoid according to claim 8, further comprising operating circuitry in electrical communication with said power source and said at least one coil segment which, during operation, can adjust the current supplied to said solenoid to adjust the strength of the magnetic holding field.

10. A solenoid according to claim 1, wherein said at least one coil segment is configured to generate a field strength to current ratio (G/A) of about 23.059 during operation.

11. A solenoid according to claim 1, wherein said solenoid is configured to generate a substantially homogeneous static magnetic holding field such that at least a portion of the magnetic holding field has a homogeneity of at least about $1 \times 10^{-3}$ cm$^{-1}$.

12. A solenoid according to claim 3, wherein gaps are present intermediate said first and second coil segments and said second and third coil segments, which, during operation, produce negligible current.

13. A solenoid according to claim 1, wherein, during operation, said cylindrical body is oriented such that the axial direction thereof is substantially vertical.

14. A solenoid according to claim 13, wherein, in operation, current is directed to flow clockwise, when viewed from the top of said cylindrical body in said at least one segment to define a magnetic holding field with a direction which is substantially aligned with the predominant direction of the earth's magnetic field.

15. A solenoid according to claim 14, wherein said cylindrical body includes an inner wall comprising a metallic material to define a columnated electrical shield extending axially therealong.

16. A solenoid according to claim 2, wherein said first and third coil segments have substantially the same first current density value, and wherein said second coil segment has a reduced second current density value relative to said first current density value.

17. A solenoid according to claim 16, wherein said second current density value is about half that of the first current density value.

18. A solenoid according to claim 2, wherein said second coil segment has a first length which is longer than the sum of the first and third coil segment lengths.

19. A solenoid according to claim 1, wherein said cylindrical body has a length of about 7 inches.

20. A solenoid according to claim 2, wherein said three coil segments are electrically connected in series.

21. A solenoid according to claim 1, further comprising a container holding a quantity of hyperpolarized gas product therein.

22. A solenoid for providing a magnetic field to shield hyperpolarized gases and to reduce the depolarization effects on such gases associated with exposure to stray magnetic field gradients or time dependent electromagnetic fields (EMI), comprising:

a cylindrical body having at least one coil segment thereon, said cylindrical body sized and configured to receive a container holding a quantity of hyperpolarized gas therein; and a power source operably associated with said at least one coil segment, wherein, in operation, current from said power source is directed into said solenoid at said at least one coil segment to generate a magnetic holding field having sufficient homogeneity and strength to shield a quantity of hyperpolarized gas from stray magnetic field gradients or EMI to thereby reduce the depolarization affects associated therewith, wherein said container has a gas holding chamber and a capillary stern, said capillary stem having an inner diameter and length configured and sized such that said capillary stem inhibits the movement of said hyperpolarized gas product from said gas holding chamber.

23. A solenoid according to claim 21, wherein said solenoid is configured to generate a magnetic field having a field strength and homogeneity selected to provide shielding for at least one of hyperpolarized $^{129}$Xe and $^{3}$He.

24. A solenoid assembly for providing a magnetic shield for hyperpolarized gases from stray magnetic field gradients or EMI to reduce the depolarization effects associated therewith, comprising:

a cylindrical body sized and configured to receive a container holding a quantity of hyperpolarized gas therein, said cylindrical body comprising:
  a first coil segment having a first coil length and a first number of windings circumferentially extending about said cylindrical body;
  a second coil segment having a second coil length and a second number of windings circumferentially extending about said cylindrical body adjacent said first coil segment; and
  a third coil segment having a third coil length and a third number of windings radially extending about said cylindrical body adjacent said second coil segment circumferentially said first coil segment;

a power source operably associated with said at least one coil segment, and a container with a quantity of hyperpolarized gas therein disposed such that at least a portion of said container resides in said cylindrical body, wherein, in operation, current from said power source is directed into said solenoid coil segments to generate a magnetic holding field having sufficient homogeneity and strength to shield the hyperpolarized gas from stray magnetic field gradients or time dependent electromagnetic fields to thereby reduce the depolarization affects associated therewith, and wherein the solenoid cylindrical body is configure to operate at ambient temperature conditions.

25. A solenoid assembly according to claim 24, wherein said first, second, and third coil segments are arranged on said cylindrical body such that each is spatially separate from the other in the axial direction.

26. A solenoid assembly according to claim 24, wherein said second coil length is greater than said first and third coil lengths.

27. A solenoid assembly according to claim 24, wherein said first and third number of windings per unit length are greater than said second number of windings.

28. A solenoid assembly according to claim 24, wherein said second coil segment has about 1.5 times the number of windings of either the first and third segments.

29. A solenoid assembly according to claim 24, wherein, in operation, said solenoid defines a magnetic holding field having a magnetic field strength of between about 2–40 Gauss.

30. A solenoid assembly according to claim 24, wherein said power source comprises a battery for portable operation.

31. A solenoid assembly according to claim 30, further comprising operating circuitry in electrical communication with said power source and said at least one coil segment which, during operation, can adjust the current supplied to said solenoid to adjust the strength of the magnetic holding field.

32. A solenoid assembly according to claim 24, wherein said solenoid is configured to generate a substantially homogeneous static magnetic holding field such that at least a portion of the magnetic holding field has a homogeneity of at least about $1 \times 10^{-3}$ cm$^{-1}$.

33. A solenoid assembly according to claim 24, wherein gaps are present intermediate said first and second coil segments and said second and third coil segments which, during operation, produce negligible current.

34. A solenoid assembly according to claim 24, wherein, during operation, said cylindrical body is oriented such that the axial direction thereof is substantially vertical.

35. A solenoid assembly according to claim 34, wherein, in operation, current is directed to flow clockwise in said coil segments, when viewed from the top of said cylindrical body, to define a magnetic holding field with a direction which is substantially aligned with the predominant direction of the earth's magnetic field.

36. A solenoid assembly according to claim 24, wherein said cylindrical body includes an inner wall comprising a metallic material to define a columnated electrical shield extending axially therealong.

37. A solenoid assembly according to claim 24, wherein said first and third coil segments have substantially the same first current density value, and wherein said second coil segment has a reduced second current density value relative to said first current density value.

38. A solenoid assembly according to claim 37, wherein said second current density value is about half that of the first current density value.

39. A solenoid assembly according to claim 24, wherein said second coil segment has a first length which is longer than the sum of the first and third coil segment lengths.

40. A solenoid assembly according to claim 24, wherein said cylindrical body has a length of about 7 inches.

41. A solenoid assembly according to claim 24, wherein said three coil segments are electrically connected in series.

42. A solenoid assembly according to claim 24, wherein said solenoid is configured to generate a magnetic field having a field strength and homogeneity selected to provide shielding for at least one of hyperpolarized $^{129}$Xe or $^{3}$He, and wherein said hyperpolarized gas comprises at least one of hyperpolarized $^{129}$Xe and $^{3}$He.

43. A solenoid according to claim 1, wherein the cylindrical body has an internal width of about at least 6.0 inches in width.

44. A solenoid according to claim 1, wherein the solenoid is configured to operate in a portable mode thereby allowing shielded hyperpolarized gas transport from one location to another.

45. A solenoid according to claim 1, wherein the low field operation is about 100 Gauss or less.

46. A solenoid assembly according to claim 24, wherein the cylindrical body has an internal width of about at least 6.0 inches in width.

47. A solenoid assembly according to claim 24, wherein the solenoid is configured to operate in a portable mode thereby allowing shielded hyperpolarized gas transport from one location to another.

48. A solenoid assembly according to claim 24, wherein, in operation, the solenoid is configured to generate a magnetic field strength of about 100 Gauss or less.

* * * * *

UNITED STATES PATENT AND TRADEMARK OFFICE
CERTIFICATE OF CORRECTION

PATENT NO. : 6,430,939 B2
DATED : August 13, 2002
INVENTOR(S) : Hasson et al.

It is certified that error appears in the above-identified patent and that said Letters Patent is hereby corrected as shown below:

Column 30,
Lines 42-46, should read -- a third coil seqment having a third coil length and a third number of windings circumferentially extending about said cylindrical body adjacent said second coil segment opposite said first coil segment; --

Signed and Sealed this

Fifteenth Day of June, 2004

JON W. DUDAS
*Acting Director of the United States Patent and Trademark Office*